(12) United States Patent
Crooke

(10) Patent No.: US 9,827,263 B2
(45) Date of Patent: Nov. 28, 2017

(54) 2'-METHOXY SUBSTITUTED OLIGOMERIC COMPOUNDS AND COMPOSITIONS FOR USE IN GENE MODULATIONS

(71) Applicant: Ionis Pharmaceuticals, Inc., Carlsbad, CA (US)

(72) Inventor: Stanley T. Crooke, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/690,120

(22) Filed: Apr. 17, 2015

(65) Prior Publication Data

US 2015/0366894 A1    Dec. 24, 2015

Related U.S. Application Data

(63) Continuation of application No. 10/701,264, filed on Nov. 4, 2003, now abandoned.

(60) Provisional application No. 60/432,760, filed on Nov. 5, 2002, provisional application No. 60/503,521, filed on Sep. 16, 2003.

(51) Int. Cl.
*A61K 31/713*    (2006.01)

(52) U.S. Cl.
CPC .................. *A61K 31/713* (2013.01)

(58) Field of Classification Search
None
See application file for complete search history.

(56) References Cited

U.S. PATENT DOCUMENTS

| 8,809,516 B2 | 8/2014 | Manoharan et al. | |
|---|---|---|---|
| 2003/0139585 A1* | 7/2003 | Uhlmann | C12N 15/111 536/23.1 |
| 2003/0143732 A1* | 7/2003 | Fosnaugh | C12N 15/113 435/325 |

* cited by examiner

*Primary Examiner* — Tracy Vivlemore
(74) *Attorney, Agent, or Firm* — Ionis Pharmaceuticals, Inc. Patent Dept.

(57) ABSTRACT

Compositions comprising first and second oligomers are provided wherein at least a portion of the first oligomer is capable of hybridizing with at least a portion of the second oligomer, at least a portion of the first oligomer is complementary to and capable of hybridizing to a selected target nucleic acid, and at least one of the first or second oligomers includes a modified sugar and/or backbone modification. In some embodiments the modification is a 2'-$OCH_3$ substituent group on a sugar moiety. Oligomer/protein compositions are also provided comprising an oligomer complementary to and capable of hybridizing to a selected target nucleic acid and at least one protein comprising at least a portion of an RNA-induced silencing complex (RISC), wherein at least one nucleotide of the oligomer has a modified sugar and/or backbone modification.

20 Claims, No Drawings

SEQUENCE LISTING

<160> NUMBER OF SEQ ID NOS: 28

<210> SEQ ID NO 1
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 1
cgagaggcgg acgggaccg                                          19

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
cgagaggcgg acgggaccgt t                                       21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
cggtcccgtc cgcctctcgt t                                       21

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tccgtcatcg ctcctcaggg                                         20

```
<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
gtgcgcgcga gcccgaaatc                                                   20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
atgcattctg cccccaagga                                                   20

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 7
caaauccaga ggcuagcagt t                                                 21

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 8
cugcuagccu cuggauuugt t                                                 21

<210> SEQ ID NO 9
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 9
cugcuagccu cuggauuugu u                                                 21

<210> SEQ ID NO 10
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 10
aaguaaggac cagagacaaa                                                   20
```

<210> SEQ ID NO 11
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 11
uuugucucug guccuuacuu                                          20

<210> SEQ ID NO 12
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 12
gucaaaucca gaggcuagca g                                        21

<210> SEQ ID NO 13
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 13
cugcuagccu cuggauuuga c                                        21

<210> SEQ ID NO 14
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 14
caaauccaga ggcuagcagu u                                        21

<210> SEQ ID NO 15
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 15
cugcuagccu cuggauuuga                                          20

<210> SEQ ID NO 16
<211> LENGTH: 17
<212> TYPE: RNA
<213> ORGANISM: Artificial sequence
<220> FEATURE:
<223> OTHER INFORMATION: Synthetic oligonucleotide

<400> SEQUENCE: 16
cuagccucug gauuuga                                             17

<210> SEQ ID NO 17
<211> LENGTH: 17
<212> TYPE: RNA
<213> ORGANISM: Artificial sequence
<220> FEATURE:

<223> OTHER INFORMATION: Synthetic oligonucleotide

<400> SEQUENCE: 17 gucucgguc cuuacuu                                                           17

<210> SEQ ID NO 18
<211> LENGTH: 17
<212> TYPE: RNA
<213> ORGANISM: Artificial sequence
<220> FEATURE:
<223> OTHER INFORMATION: Synthetic oligonucleotide

<400> SEQUENCE: 18 uuugucucu gguccuu                                                           17

<210> SEQ ID NO 19
<211> LENGTH: 17
<212> TYPE: RNA
<213> ORGANISM: Artificial sequence
<220> FEATURE:
<223> OTHER INFORMATION: Synthetic oligonucleotide

<400> SEQUENCE: 19
cugguccuua cuuccccc                                                         17

<210> SEQ ID NO 20
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 20
uuugucucug guccuuacuu                                                       20

<210> SEQ ID NO 21
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 21 ucucggucc uuacuucccc                                                        20

<210> SEQ ID NO 22
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 22
uuugucucug guccuuacuu                                                       20

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 23
cugcuagccu cuggauuugt t          21

<210> SEQ ID NO 24
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 24
cugcuagccu cuggauuugu u          21

<210> SEQ ID NO 25
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: bases at these positions are RNA

<400> SEQUENCE: 25
cugcuagccu cuggauuugu t          21

<210> SEQ ID NO 26
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 26
cugcuagccu cuggauuuga c          21

<210> SEQ ID NO 27
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: bases at these positions are RNA

<400> SEQUENCE: 27
cugcuagccu cuggauuugu t          21

<210> SEQ ID NO 28
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 28
uuugucucug guccuuacuu          20

2'-METHOXY SUBSTITUTED OLIGOMERIC COMPOUNDS AND COMPOSITIONS FOR USE IN GENE MODULATIONS

SEQUENCE LISTING

The present application is being filed along with a Sequence Listing in electronic format. The Sequence Listing is provided as a file entitled ISIS5314C1SEQ_ST25.txt created Apr. 17, 2015, which is 8 Kb in size. The information in the electronic format of the sequence listing is incorporated herein by reference in its entirety.

FIELD OF THE INVENTION

The present invention provides modified oligomers that modulate gene expression via a RNA interference pathway. The oligomers of the invention include one or more modifications thereon resulting in differences in various physical properties and attributes compared to wild type nucleic acids. The modified oligomers are used alone or in compositions to modulate the targeted nucleic acids. In preferred embodiments of the invention, the modifications include a 2' substituent group on at least one sugar moiety of the oligomer.

BACKGROUND OF THE INVENTION

In many species, introduction of double-stranded RNA (dsRNA) induces potent and specific gene silencing. This phenomenon occurs in both plants and animals and has roles in viral defense and transposon silencing mechanisms. This phenomenon was originally described more than a decade ago by researchers working with the *petunia* flower. While trying to deepen the purple color of these flowers, Jorgensen et al. introduced a pigment-producing gene under the control of a powerful promoter. Instead of the expected deep purple color, many of the flowers appeared variegated or even white. Jorgensen named the observed phenomenon "cosuppression", since the expression of both the introduced gene and the homologous endogenous gene was suppressed (Napoli et al., *Plant Cell*, 1990, 2, 279-289; Jorgensen et al., *Plant Mol. Biol.*, 1996, 31, 957-973).

Cosuppression has since been found to occur in many species of plants, fungi, and has been particularly well characterized in *Neurospora crassa*, where it is known as "quelling" (Cogoni and Macino, *Genes Dev.* 2000, 10, 638-643; Guru, *Nature*, 2000, 404, 804-808).

The first evidence that dsRNA could lead to gene silencing in animals came from work in the nematode, *Caenorhabditis elegans*. In 1995, researchers Guo and Kemphues were attempting to use antisense RNA to shut down expression of the par-1 gene in order to assess its function. As expected, injection of the antisense RNA disrupted expression of par-1, but quizzically, injection of the sense-strand control also disrupted expression (Guo and Kempheus, *Cell*, 1995, 81, 611-620). This result was a puzzle until Fire et al. injected dsRNA (a mixture of both sense and antisense strands) into *C. elegans*. This injection resulted in much more efficient silencing than injection of either the sense or the antisense strands alone. Injection of just a few molecules of dsRNA per cell was sufficient to completely silence the homologous gene's expression. Furthermore, injection of dsRNA into the gut of the worm caused gene silencing not only throughout the worm, but also in first generation offspring (Fire et al., *Nature*, 1998, 391, 806-811).

The potency of this phenomenon led Timmons and Fire to explore the limits of the dsRNA effects by feeding nematodes bacteria that had been engineered to express dsRNA homologous to the *C. elegans* unc-22 gene. Surprisingly, these worms developed an unc-22 null-like phenotype (Timmons and Fire, *Nature* 1998, 395, 854; Timmons et al., *Gene*, 2001, 263, 103-112). Further work showed that soaking worms in dsRNA was also able to induce silencing (Tabara et al., *Science*, 1998, 282, 430-431). PCT publication WO 01/48183 discloses methods of inhibiting expression of a target gene in a nematode worm involving feeding to the worm a food organism which is capable of producing a double-stranded RNA structure having a nucleotide sequence substantially identical to a portion of the target gene following ingestion of the food organism by the nematode, or by introducing a DNA capable of producing the double-stranded RNA structure (Bogaert et al., 2001).

The posttranscriptional gene silencing defined in *Caenorhabditis elegans* resulting from exposure to double-stranded RNA (dsRNA) has since been designated as RNA interference (RNAi). This term has come to generalize all forms of gene silencing involving dsRNA leading to the sequence-specific reduction of endogenous targeted mRNA levels; unlike co-suppression, in which transgenic DNA leads to silencing of both the transgene and the endogenous gene.

Introduction of exogenous double-stranded RNA (dsRNA) into *Caenorhabditis elegans* has been shown to specifically and potently disrupt the activity of genes containing homologous sequences. Montgomery et al. suggests that the primary interference affects of dsRNA are posttranscriptional. This conclusion being derived from examination of the primary DNA sequence after dsRNA-mediated interference and a finding of no evidence of alterations, followed by studies involving alteration of an upstream operon having no effect on the activity of its downstream gene. These results argue against an effect on initiation or elongation of transcription. Finally using in situ hybridization they observed that dsRNA-mediated interference produced a substantial, although not complete, reduction in accumulation of nascent transcripts in the nucleus, while cytoplasmic accumulation of transcripts was virtually eliminated. These results indicate that the endogenous mRNA is the primary target for interference and suggest a mechanism that degrades the targeted mRNA before translation can occur. It was also found that this mechanism is not dependent on the SMG system, an mRNA surveillance system in *C. elegans* responsible for targeting and destroying aberrant messages. The authors further suggest a model of how dsRNA might function as a catalytic mechanism to target homologous mRNAs for degradation. (Montgomery et al., *Proc. Natl. Acad. Sci. USA*, 1998, 95, 15502-15507).

Recently, the development of a cell-free system from syncytial blastoderm *Drosophila* embryos, which recapitulates many of the features of RNAi, has been reported. The interference observed in this reaction is sequence specific, is promoted by dsRNA but not single-stranded RNA, functions by specific mRNA degradation, and requires a minimum length of dsRNA. Furthermore, preincubation of dsRNA potentiates its activity demonstrating that RNAi can be mediated by sequence-specific processes in soluble reactions (Tuschl et al., *Genes Dev.*, 1999, 13, 3191-3197).

In subsequent experiments, Tuschl et al, using the *Drosophila* in vitro system, demonstrated that 21- and 22-nt RNA fragments are the sequence-specific mediators of RNAi. These fragments, which they termed short interfering RNAs (siRNAs), were shown to be generated by an RNase III-like processing reaction from long dsRNA. They also showed that chemically synthesized siRNA duplexes with overhanging 3' ends mediate efficient target RNA cleavage in the Drosophila lysate, and that the cleavage site is located near the center of the region spanned by the guiding siRNA. In addition, they suggest that the direction of dsRNA processing determines whether sense or antisense target RNA can be cleaved by the siRNA-protein complex (Elbashir et al., *Genes Dev.*, 2001, 15, 188-200). Further characterization of the suppression of expression of endogenous and heterologous genes caused by the 21-23 nucleotide siRNAs have been investigated in several mammalian cell lines, including human embryonic kidney (293) and HeLa cells (Elbashir et al., *Nature*, 2001, 411, 494-498).

The *Drosophila* embryo extract system has been exploited, using green fluorescent protein and luciferase tagged siRNAs, to demonstrate that siRNAs can serve as primers to transform the target mRNA into dsRNA. The nascent dsRNA is degraded to eliminate the incorporated target mRNA while generating new siRNAs in a cycle of dsRNA synthesis and degradation. Evidence is also presented that mRNA-dependent siRNA incorporation to form dsRNA is carried out by an RNA-dependent RNA polymerase activity (RdRP) (Lipardi et al., *Cell*, 2001, 107, 297-307).

The involvement of an RNA-directed RNA polymerase and siRNA primers as reported by Lipardi et al. (Lipardi et al., *Cell*, 2001, 107, 297-307) is one of the many intriguing features of gene silencing by RNA interference. This suggests an apparent catalytic nature to the phenomenon. New biochemical and genetic evidence reported by Nishikura et al. also shows that an RNA-directed RNA polymerase chain reaction, primed by siRNA, amplifies the interference caused by a small amount of "trigger" dsRNA (Nishikura, *Cell*, 2001, 107, 415-418).

Investigating the role of "trigger" RNA amplification during RNA interference (RNAi) in *Caenorhabditis elegans*, Sijen et al revealed a substantial fraction of siRNAs that cannot derive directly from input dsRNA. Instead, a population of siRNAs (termed secondary siRNAs) appeared to derive from the action of the previously reported cellular RNA-directed RNA polymerase (RdRP) on mRNAs that are being targeted by the RNAi mechanism. The distribution of secondary siRNAs exhibited a distinct polarity (5'-3; on the antisense strand), suggesting a cyclic amplification process in which RdRP is primed by existing siRNAs. This amplification mechanism substantially augmented the potency of RNAi-based surveillance, while ensuring that the RNAi machinery will focus on expressed mRNAs (Sijen et al., *Cell*, 2001, 107, 465-476).

Most recently, Tijsterman et al. have shown that, in fact, single-stranded RNA oligomers of antisense polarity can be potent inducers of gene silencing. As is the case for co-suppression, they showed that antisense RNAs act independently of the RNAi genes rde-1 and rde-4 but require the mutator/RNAi gene mut-7 and a putative DEAD box RNA helicase, mut-14. According to the authors, their data favor the hypothesis that gene silencing is accomplished by RNA primer extension using the mRNA as template, leading to dsRNA that is subsequently degraded suggesting that single-stranded RNA oligomers are ultimately responsible for the RNAi phenomenon (Tijsterman et al., *Science*, 2002, 295, 694-697).

Several recent publications have described the structural requirements for the dsRNA trigger required for RNAi activity. Recent reports have indicated that ideal dsRNA sequences are 21 nt in length containing 2 nt 3'-end overhangs (Elbashir et al, EMBO (2001), 20, 6877-6887, Sabine Brantl, *Biochimica et Biophysica Acta*, 2002, 1575, 15-25.) In this system, substitution of the 4 nucleosides from the 3'-end with 2'-deoxynucleosides has been demonstrated to not affect activity. On the other hand, substitution with 2'-deoxynucleosides or 2'-OCH$_3$-nucleosides throughout the sequence (sense or antisense) was shown to be deleterious to RNAi activity.

Investigation of the structural requirements for RNA silencing in *C. elegans* has demonstrated modification of the internucleotide linkage (phosphorothioate) to not interfere with activity (Parrish et al., *Molecular Cell*, 2000, 6, 1077-1087.) It was also shown by Parrish et al., that chemical modification like 2'-amino or 5-iodouridine are well tolerated in the sense strand but not the antisense strand of the dsRNA suggesting differing roles for the 2 strands in RNAi. Base modification such as guanine to inosine (where one hydrogen bond is lost) has been demonstrated to decrease RNAi activity independently of the position of the modification (sense or antisense). Some "position independent" loss of activity has been observed following the introduction of mismatches in the dsRNA trigger. Some types of modifications, for example introduction of sterically demanding bases such as 5-iodoU, have been shown to be deleterious to RNAi activity when positioned in the antisense strand, whereas modifications positioned in the sense strand were shown to be less detrimental to RNAi activity. As was the case for the 21 nt dsRNA sequences, RNA-DNA heteroduplexes did not serve as triggers for RNAi. However, dsRNA containing 2'-F-2'-deoxynucleosides appeared to be efficient in triggering RNAi response independent of the position (sense or antisense) of the 2'-F-2'-deoxynucleosides.

In one study the reduction of gene expression was studied using electroporated dsRNA and a 25mer morpholino oligomer in post implantation mouse embryos (Mellitzer et al., *Mehanisms of Development*, 2002, 118, 57-63). The morpholino oligomer did show activity but was not as effective as the dsRNA.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

U.S. Pat. Nos. 5,898,031 and 6,107,094, each of which is commonly owned with this application and each of which is herein incorporated by reference, describe certain oligonucleotide having RNA like properties. When hybridized with RNA, these oligonucleotides serve as substrates for a dsRNase enzyme with resultant cleavage of the RNA by the enzyme.

In another recently published paper (Martinez et al., *Cell*, 2002, 110, 563-574) it was shown that single stranded as well as double stranded siRNA resides in the RNA-induced silencing complex (RISC) together with eIF2C1 and eIf2C2 (human GERp950) Argonaute proteins. The activity of 5'-phosphorylated single stranded siRNA was comparable to the double stranded siRNA in the system studied. In a related study, the inclusion of a 5'-phosphate moiety was shown to enhance activity of siRNA's in vivo in Drosophilia embryos (Boutla, et al., Curr. Biol., 2001, 11, 1776-1780). In another study, it was reported that the 5'-phosphate was required for siRNA function in human HeLa cells (Schwarz et al., *Molecular Cell*, 2002, 10, 537-548).

In yet another recently published paper (Chiu et al., *Molecular Cell*, 2002, 10, 549-561) it was shown that the 5'-hydroxyl group of the siRNA is essential as it is phosphorylated for activity while the 3'-hydroxyl group is not essential and tolerates substitute groups such as biotin. It was further shown that bulge structures in one or both of the sense or antisense strands either abolished or severely lowered the activity relative to the unmodified siRNA duplex. Also shown was severe lowering of activity when psoralen was used to cross link an siRNA duplex.

Like the RNAse H pathway, the RNA interference pathway for modulation of gene expression is an effective means for modulating the levels of specific gene products and, thus, would be useful in a number of therapeutic, diagnostic, and research applications involving gene silencing. The present invention therefore provides oligomeric compounds useful for modulating gene expression pathways, including those relying on mechanisms of action such as RNA interference and dsRNA enzymes, as well as antisense and non-antisense mechanisms. One having skill in the art, once armed with this disclosure will be able, without undue experimentation, to identify preferred oligonucleotide compounds for these uses.

SUMMARY OF THE INVENTION

In certain aspects, the invention relates to compositions comprising a first oligomer and a second oligomer, each having linked nucleosidic bases. At least a portion of the first oligomer is capable of hybridizing with at least a portion of the second oligomer, at least a portion of the first oligomer is complementary to and capable of hybridizing to a selected target nucleic acid, and at least one of the first and second oligomers includes at least one sugar moiety having a 2'-OCH$_3$ substituent group.

In some embodiments, the first and second oligomers are a complementary pair of siRNA oligomers. In certain embodiments, the first and second oligomers are an antisense/sense pair of oligomers. In some compositions, each of the first and second oligomers has about 0 to about 40 linked nucleosides. In other compositions, each of the first and second oligomers has about 18 to about 30 linked nucleosides. In yet other compositions, each of the first and second oligomers has about 21 to about 24 linked nucleosides.

In certain aspects, the first oligomer is an antisense oligomer. In other aspects, the second oligomer comprises a sense oligomer. In some embodiments, the second oligomer has a plurality of ribose nucleoside units. In still other embodiments, the first oligomer includes said 2'-OCH$_3$ substituent group.

In some preferred embodiments, the first oligomer comprises a 3' terminus and a 5' terminus, said 5' terminus comprising a hydroxy terminal group. In other preferred embodiments, the 2'-OCH$_3$ substituent group extend from the 3' terminus of the first oligomer through the fourth, third, or penultimate nucleoside from the 5' terminus.

In certain preferred embodiments, the first oligomer comprises a 3' terminus and a 5' terminus, wherein the nucleoside at the 5' terminus comprises a 2'-OCH$_3$ substituent group. In some of these compositions, the 5' terminus comprises a 3'-phosphate terminal group.

In some aspects, the first oligomer is a chimeric oligomeric compound. Certain chimeric compositions are a gapmer, an inverted gapmer, a 3'-hemimer, a 5'-hemimer or a blockmer. In some aspects, the chimeric oligomeric compound comprises two terminal RNA segments having nucleosides of a first type and an internal RNA segment having nucleosides of a second type and where said nucleosides of said first type are different from said nucleosides of said second type. In certain preferred embodiments, the nucleosides of said first type includes a 2'-OCH$_3$ substitutent group.

In other embodiments, the invention is directed to oligonucleomer/protein compositions comprising an oligomer complementary to and capable of hybridizing to a selected target nucleic acid, and at least one protein comprising at least a portion of a RNA-induced silencing complex (RISC). The oligomer includes at least one nucleoside having a 2'-OCH$_3$ substitutent group on the sugar moiety.

Also provided by the present invention are pharmaceutical compositions comprising any of the above compositions or oligomeric compounds and a pharmaceutically acceptable carrier.

Methods for modulating the expression of a target nucleic acid in a cell are also provided, wherein the methods comprise contacting the cell with any of the above compositions or oligomeric compounds.

Methods of treating or preventing a disease or condition associated with a target nucleic acid are also provided, wherein the methods comprise administering to a patient having or predisposed to the disease or condition a therapeutically effective amount of any of the above compositions or oligomeric compounds.

DETAILED DESCRIPTION OF THE INVENTION

The present invention provides oligomeric compounds useful in the modulation of gene expression. Although not intending to be bound by theory, oligomeric compounds of the invention modulate gene expression by hybridizing to a nucleic acid target resulting in loss of normal function of the target nucleic acid. As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In a preferred embodiment of this invention modulation of gene expression is effected via modulation of a RNA associated with the particular gene RNA.

The invention provides for modulation of a target nucleic acid that is a messenger RNA. The messenger RNA is degraded by the RNA interference mechanism as well as other mechanisms in which double stranded RNA/RNA structures are recognized and degraded, cleaved or otherwise rendered inoperable.

The functions of RNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, "modulation" and "modulation of expression" mean either an increase (stimulation) or a decrease (inhibition) in the amount or levels of a nucleic acid molecule encoding the gene, e.g., DNA or RNA Inhibition is often the preferred form of modulation of expression and mRNA is often a preferred target nucleic acid.

Compounds of the Invention

The compounds of the invention include oligomeric compounds that comprise at least one monomeric unit that has a 2'-OCH$_3$ substituent group on the sugar moiety. 2'-Sugar substituents are described in more detail in U.S. Pat. Nos. 5,670,633, 5,914,396, 6,005,087, 6,222,025, 6,307,040, 6,531,584 and in U.S. patent application Ser. No. 10/444,628. The disclosure of each of these patents and applications is incorporated herein by reference in its entirety.

In some compositions, one or more sugars may contain a 2'-substitutent other than 2'-OCH$_3$. In certain embodiments, these substituent group may be halogen, amino, trifluoroalkyl, trifluoroalkoxy, azido, aminooxy, alkyl, alkenyl, alkynyl, O-, S-, or N(R*)-alkyl; O-, S-, or N(R*)-alkenyl; O-, S- or N(R*)-alkynyl; O-, S- or N-aryl, O-, S-, or N(R*)-aralkyl; wherein said alkyl, alkenyl, alkynyl, aryl and aralkyl may be substituted or unsubstituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl; and said substituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl comprising substitution with hydroxy, alkoxy, thioalkoxy, phthalimido, halogen, amino, keto, carboxyl, nitro, nitroso, cyano, aryl, haloalkyl, haloalkoxy, imidazole, azido, hydrazino, aminooxy, isocyanato, sulfoxide, sulfone, disulfide, silyl, heterocycle, carbocycle, an intercalator, a reporter group, a conjugate, a polyamine, a polyamide, a polyalkylene glycol, or a polyether of the formula (—O-alkyl)$_m$, where m is 1 to about 10; and R* is hydrogen, or a protecting group.

As discussed above, the 2' substituent may be a halogen. In some preferred embodiments the halogen is F. Certain oligonucleosides that are N3'→P5' phosphoramidates having 2' fluoro substituents have been shown to have superior acid stability. These compositions can be made by procedures taught is U.S. Pat. No. 5,684,143, the disclosure of which is incorporated herein in its entirety.

Some preferred substituents are 2'-O-alkyl substituents. These alkyl groups include lower alkyl groups having from about 1 to about 6 carbon atoms. In some preferred embodiments, the alkyl is a $C_2$-$C_6$ group. Other 2' substituent groups include 2'-methoxyethoxy (MOE, 2'-OCH$_2$CH$_2$OCH$_3$) and 2'-O-[2-(2-N,N-dimethylaminoethyl)oxyethyl]. These substituents are described in U.S. Pat. Nos. 6,043,352 and 6,005,094, the disclosures of which are incorporated herein by reference in their entirety.

In other embodiments, the 2' substituent is —O—R$^{26}$-thio-R$^{26}$ or —C—R$^{26}$-thio-R$^{26}$, wherein said R$^{26}$ is independently a compound selected from a group consisting of alkyl, allyl, alkenyl, alkynyl, aryl, alkylaryl, carbocyclic aryl, heterocyclic aryl, amide and ester. In some embodiments, R$^{26}$ is alkyl, allyl, alkenyl, alkynyl, aryl, alkylaryl, carbocyclic aryl, or heterocyclic aryl. In certain embodiments, the 2' substituent is 2'-O-methylthiomethyl. In other embodiments, the 2' substituent is 2'-O-methylthioethyl. These substituents are described in U.S. Pat. Nos. 5,716,824, 5,840,876 and 6,239,272, the disclosures of which are incorporated by reference herein in their entirety.

In certain embodiments, the 2' substituent is cyano, fluoromethyl, thioalkoxyl, fluoroalkoxyl, alkylsulfinyl, alkylsulfonyl, allyloxy or alkeneoxy. In other embodiments, the 2'-substituent is 2'-alkylsulfinyl or alkylsulfonyl. In other preferred embodiments, the 2'-substituent is 2'-thioalkoxyl, preferably, a 2'-S—(C$_1$-C$_{20}$ alkyl) substituent. These substituents are described in U.S. Pat. No. 5,859,221, the disclosure of which is incorporated herein by reference.

Some 2' substituents useful in the invention are of the formula —X—Y. X is O, S, NR$^{27}$, or CR$^{27}$$_2$ wherein each R is independently H or C$_{1-6}$ alkyl. Y is a linker moiety, a drug residue optionally attached through a linker moiety, a label optionally attached through a linker moiety, or a property-affecting group optionally attached through a linker moiety. In some embodiments, Y is a drug moiety. In certain embodiments, the drug moiety is selected from the group consisting of netropsin, anthramycin, quinoxaline antibiotics, actinomycin, and pyrrolo (1-4) benzodiazepine. In other embodiments, Y is substituted or unsubstituted alkyl (C$_{2-20}$), substituted or unsubstituted alkenyl (C$_{2-20}$), substituted or unsubstituted aryl (C$_{6-20}$), wherein the substituents are selected from the group consisting of a hydroxyl, an amino, a mercaptyl, a carboxy or a keto moiety, —CH$_2$COOH, —CH$_2$COONH$_2$, —CH$_2$COOEt, —CH$_2$CONHCH$_2$CH$_2$NH$_2$ and SiR$^{28}$$_3$ wherein R$^{28}$ is alkyl (C$_{2-6}$). In certain preferred embodiments, X is O or S. These substituents are described in U.S. Pat. Nos. 5,466,786 and 5,792,847, the disclosures of which are incorporated herein by reference in their entirety.

Certain 2' substituents are of the formula:
-G1-G2-G3 where G1 is a bivalent linker, G2 is an aryl or heteroaryl or aryl or heteroaryl containing group and G3 is an RNA cleaving moiety having, for example, general acid/base properties. In certain further preferred embodiments of the inventions, G3 further includes an electrophilic catalyst.

The bivalent liker may be a mono- or polyatomic linker. In some embodiments, the bivalent linker is of the formula -G$^{11}$-G$^{12}$. G$^{11}$ contains a heteroatom and G$^{12}$ contains an alkyl, alkenyl or alkynyl group. Preferred heteroatoms include O, S, and N—H or N-alkyl. In some embodiments, the linker may be methylene groups—i.e., —(CH$_2$)$_n$— or may include heteroatoms and functional groups, e.g., —CH$_2$OCH$_2$CH$_2$O— or —CH$_2$O—CH$_2$CH$_2$NH— or —COOCH$_2$CH$_2$O—. In certain embodiments of the invention, G1 connects to the internucleoside linkage, i.e. the sugar linking group.

G2 preferably is a polycyclic moiety having from 2 to 6 rings, at least 2 of said rings being joined to form an electronically conjugated system. Representative G2 groups include naphthalene, anthracene, phenanthrene, benzonaphthalene, fluorene, carbazole, pyrido[4,3-b]carbazole, acridine, pyrene, anthraquinone, quinoline, phenylquinoline, xanthene or 2,7-diazaanthracene groups. Structures of this type preferably act as intercalators. Other intercalators believed to be useful are described by Denny, Anti-Cancer Drug Design 1989, 4, 241.

RNA-cleaving group G3 can be a functionality that has both general acid and general base characteristics. It also can possess electrophilic catalytic characteristics. It can further possess metal ion coordinating characteristics. Such substituents are described in U.S. Pat. No. 6,358,931, whose disclosure is incorporated by reference herein in its entirety.

The 2' substituent may be of the formula —O-G1-G2-G3 where G1 is alkyl, alkenyl, or alkynyl; G2 is an aryl; and G3 includes at least one imidazole. In some preferred embodiments, G3 is an imidazole or a bis-imidazole moiety. In other embodiments, G1-G2-G3 is an alkynyl moiety. These substituents are described in U.S. Pat. No. 5,514,786, whose disclosure is incorporated herein by reference in its entirety.

Some useful 2' substituents are of the formula —C(X)—N(R$^{29}$)(R$^{30}$) where:
R$^{29}$ and R$^{30}$, independently, are H, R$^{33}$, R$^{34}$, an amine protecting group or have formula R$^{33}$—N(R$^{31}$)(R$^{32}$), C(X)—R$^{33}$, C(X)—R$^{34}$—R$^{33}$, C(X)-Q-R$^{34}$—R$^{33}$, or C(X)-

Q-R$^{33}$; R$^{31}$ and R$^{32}$, independently, are H, R$^{33}$, R$^{34}$, an amine protecting group or have formula C(X)—R$^{33}$, C(X)—R$^{34}$—R$^{33}$, C(X)-Q-R$^{34}$—R$^{33}$, or C(X)-Q-R$^{33}$; R$_{33}$ is a steroid molecule, biotin, dinitrophenyl, a fluorescein dye, a lipophilic molecule, a reporter enzyme, a peptide, a protein, includes folic acid, or has formula -Q-(CH$_2$CH$_2$-Q-)$_x$—R$^{35}$;
R$^{34}$ is alkyl having from 1 to about 10 carbon atoms;
X is O or S;
each Q is, independently, is NH, O, or S;
R$^{35}$ is H, R$^{34}$, C(O)OH, C(O)OR$^{34}$, C(O)R$^{41}$, R$^{34}$—N$_3$, or R$^{34}$—NH$_2$;
R$^{41}$ is Cl, Br, I, SO$_2$R$^{42}$ or has structure:

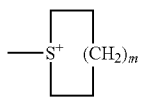

m is 2 or 7; and
R$^{42}$ alkyl having 1 to about 10 carbon atoms.

In some embodiments, R$^{34}$ is alkyl having 1 to about 10 carbon atoms, preferably having 6 carbon atoms. In other embodiments, R$^{29}$ is H and R$^{30}$ is R$^{33}$. Some compounds are such that R$^{29}$ is H and R$^{30}$ is alkyl having 1 to about 10 carbon atoms, preferably 1 or 2 carbon atoms. In certain embodiments, R$^{29}$ and R$^{30}$, together, are phthalimido. In other embodiments, R$^{29}$ is H and R$^{30}$ is R$^{34}$—N(R$^{31}$)(R$^{32}$). These compounds are described in U.S. Pat. No. 6,111,085, whose disclosure is incorporated herein by reference in its entirety.

The sugar substituent may be a 2'-aminoalkoxy or a 2'-imidazolylalkoxy substituent, wherein the alkoxy moiety of said substituent is C$_1$-C$_{20}$. In some embodiments the substituent is 2'-O-(aminoprop-3-yl) or 2'-O-(aminobut-4-yl). In other embodiments, the substituent is 2'-O→(imidazol-1-yl) prop-3-yl or 2'-O→(imidazol-1-yl) but-4-yl. See, for example, U.S. Pat. No. 5,872,232, which is incorporated herein by reference in its entirety.

Certain 2' modifications are groups of the formula:

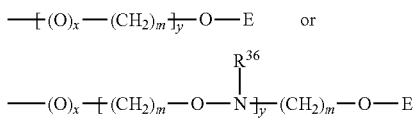

where m is from 0 to 10; y is from 1 to 10; x is 1; E is N(R$^{37}$)(R$^{38}$) or N=C(R$^{37}$)(R$^{38}$); and each of R$^{36}$, R$^{37}$ and R$^{38}$ is, independently, H, C$_1$-C$_{10}$ alkyl, and an amino protecting group, or R$^{37}$ and R$^{38}$ together, are an amino protecting group or wherein R$^{37}$ and R$^{38}$ are joined in a C$_4$-C$_{10}$ ring structure that can include at least one heteroatom selected from N and O. In certain embodiments, R$^{37}$ and R$^{38}$ are independently H or C$_1$-C$_{10}$ alkyl. In other embodiments R$^{37}$ and R$^{38}$ are joined in a C$_4$-C$_{10}$ ring structure that optionally includes one or more heteroatoms selected from N and O. Some compounds of the invention comprise a ring structure that is an imidazolyl ring, a piperidinyl ring, a morpholinyl ring or a substituted piperazinyl ring. Certain piperazine may be optionally substituted with a C$_1$-C$_{12}$ alkyl. These substituent groups may be produced by methods taught by U.S. Pat. Nos. 6,127,533 and 6,172,209 the disclosures of which are incorporated by reference herein in their entirety.

In certain embodiments, the 2' substituent is of the formula:

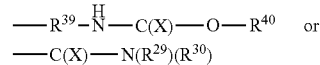

where R$^{39}$ is alkyl having from 1 to about 10 carbon atoms or (CH$_2$—CH$_2$-Q)$_x$;
R$^{40}$ is alkenyl having 2 to about 10 carbon atoms;
R$^{29}$ and R$^{30}$, independently, are H, R$^{33}$, R$^{39}$, an amine protecting group or have formula R$^{39}$—N(R$^{31}$)(R$^{32}$), C(X)—R$^{33}$, C(X)—R$^{39}$—R$^{33}$, C(X)-Q-R$^{39}$—R$^{33}$, or C(X)-Q-R$^{33}$; R$^{31}$ and R$^{32}$, independently, are H, R$^{33}$, R$^{39}$, an amine protecting group or have formula C(X)—R$^{33}$, C(X)—R$^{39}$—R$^{33}$, C(X)-Q-R$^{39}$—R$^{33}$, or C(X)-Q-R$^{33}$;
R$^{33}$ is a steroid molecule, a reporter molecule, a lipophilic molecule, a reporter enzyme, a peptide, a protein, includes folic acid, or has formula -Q-(CH$_2$CH$_2$-Q-)$_x$-R$^{35}$;
X is O or S;
each Q is, independently, is NH, O, or S;
x is 1 to about 200;
R$^{35}$ is H, R$^{39}$, C(O)OH, C(O)OR$^{39}$, C(O)R$^{41}$, R$^{39}$—N$_3$, or R$^{39}$—NH$_2$;
R$^{41}$ is Cl, Br, I, SO$_2$R$^{42}$ or has structure:

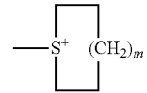

m is 2 or 7; and R$_{42}$ is an alkyl having 1 to about 10 carbon atoms.

In some embodiments, R$^{39}$ is alkyl having 6 carbon atoms. In certain embodiments, R$^{40}$ is 2-propenyl. In other embodiments, R$^{29}$ is H and R$^{30}$ is H. In yet other embodiments, R$^{29}$ is H and R$^{30}$ is R$^{33}$. In some compositions, R$^{29}$ is H and R$^{30}$ is alkyl having 1 to about 10 carbon atoms. In certain embodiments, R$^{29}$ and R$^{30}$, together, are phthalimido. In other embodiments, R$^{29}$ is H and R$^{30}$ is R$^{39}$—N(R$^{31}$)(R$^{32}$). In certain compositions of the invention, R$^{31}$ is H and R$^{32}$ is R$^{33}$. In other compositions, R$^{31}$ is H and R$^{32}$ is alkyl having 1 to about 10 carbon atoms. In yet other compositions, R$^{30}$ is H and R$^{32}$ is an alkyl having 1 or 2 carbon atoms. In yet other compositions, R$^{31}$ and R$^{32}$, together, are phthalimido. These substituents may be synthesized by methods taught by U.S. Pat. No. 6,166,188, the disclosure of which is incorporated herein by reference in its entirety.

Some 2' substituents are of the formula:

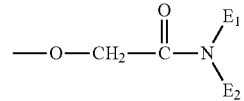

wherein each E$_1$ and E$_2$ is, independently, H, C$_1$-C$_{10}$ alkyl, C$_2$-C$_{10}$ alkenyl, C$_2$-C$_{10}$ alkynyl, C$_6$-C$_{14}$ aryl, (CH$_2$)$_m$—S—R$^{43}$ where m is from 1 to 10, —{(CH$_2$)$_{nn}$—N(H)}$_{nnn}$—(CH$_2$)$_{nn}$NH$_2$ where each nn is an integer from 2 to 4 and nnn is an integer from 2 to 10, a polypeptide having from 2 to 10 peptide linked amino acids, a folic acid moiety optionally bearing a linking group attaching said folic acid moiety from the α or γ carboxyl group to the 2'-substituent wherein said linking group is —N(H)—(CH$_2$)$_6$—, or a cholesterol moiety optionally bearing a linking group attaching said cholesterol moiety from the hydroxyl group to the 2'-substituent, wherein said linking group is —C(=O)—N(H)—(CH$_2$)$_6$—; and R$^{43}$ is H, C$_1$-C$_{10}$ alkyl, C$_2$-C$_{10}$ alkenyl, C$_2$-C$_{10}$ alkynyl, C$_6$-C$_{14}$ aryl or a thio protecting group. In some embodiments, each E$_1$ and E$_2$ is independently C$_1$-C$_{10}$ alkyl.

In some embodiments, each E$_1$ and E$_2$ is, independently, C$_1$-C$_{10}$ alkyl, or one of E$_1$ and E$_2$ is H and the other of E$_1$ and E$_2$ is —CH$_3$;

or each E$_1$ and E$_2$ is, independently, H, —(CH$_2$)$_m$—S—R$^{43}$ where m is from 1 to 10, —{(CH$_2$)$_{nn}$—N(H)}$_{nnn}$—(CH$_2$)$_{nn}$NH$_2$ where each nn is from 2 to 4 and nnn is from 2 to 10, a polypeptide having from 2 to 10 peptide linked amino acids, a folic acid moiety optionally bearing a linking group attaching said folic acid moiety from the α or γ carboxyl group to the 2'-substituent wherein said linking group is —N(H)—(CH$_2$)$_6$—, or a cholesterol moiety optionally bearing a linking group attaching said cholesterol moiety from the hydroxyl group to the 2'-substituent, wherein said linking group is —C(=O)—N(H)—(CH$_2$)$_6$—, provided that only one of E$_1$ and E$_2$ is H; and R$^{43}$ is H, C$_1$-C$_{10}$ alkyl, C$_2$-C$_{10}$ alkenyl, C$_2$-C$_{10}$ alkynyl, C$_6$-C$_{14}$ aryl or a thio protecting group.

In certain embodiments, E$_1$ is H and E$_2$ is —(CH$_2$)$_m$—S—R$^{43}$. In other embodiments, R$^{43}$ is C$_1$-C$_{10}$ alkyl. Further embodiments are those where R$^{43}$ is methyl. In yet other embodiments, E$_2$ is {(CH$_2$)$_{nn}$—N(H)}$_{nnn}$(CH$_2$)$_{nn}$NH$_2$ where each nn is from 2 to 4 and nnn is from 2 to 10. In some compositions, E$_2$ is —(CH$_2$)$_3$—N(H)—(CH$_2$)$_4$—N(H)—(CH$_2$)$_3$—NH$_2$ or —(CH$_2$)$_4$—N(H)—(CH$_2$)$_3$—NH$_2$. In certain embodiments, E$_2$ is said polypeptide. In some embodiments, the polypeptide is Lys-Tyr-Lys, Lys-Trp-Lys or Lys-Lys-Lys-Lys. In yet other embodiments, E$_2$ is a linked folic acid or 5-methyl-tetrahydrofolic acid moiety. In further embodiments, E$_2$ is a cholesterol moiety. These substituents may be made may methods disclosed in U.S. Pat. No. 6,147,200, whose disclosure is incorporated by reference herein in its entirety.

Other 2' substituent groups of the invention are of the formula:

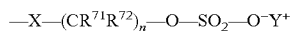

—X—(CR$^{71}$R$^{72}$)$_n$—O—SO$_2$—O$^-$Y$^+$ where X is a O, S, or N; R$^{71}$ and R$^{72}$ are independently H, alkyl, aryl, O-alkyl, O-aryl, carboxylic acid, amide, ester, halogen, trifluoromethyl, or amine; n is an integer from about 2 to about 10; and, Y is H, Li, Na, K, Cs or an amine. The synthesis of compounds with these substituent groups is described in U.S. Pat. No. 6,227,982, the disclosure of which is incorporated herein in its entirety.

Some 2' substituents are of the formula:

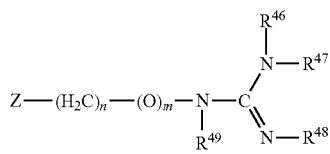

where:
each Z is, independently, a single bond, 0, N or S;
each R$^{46}$, R$^{47}$, R$^{48}$, and R$^{49}$ is, independently, hydrogen, C(O)R$^{50}$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or R$^{46}$ and R$^{47}$, together, are R$^{51}$;
each R$^{50}$ is, independently, substituted or unsubstituted C$_1$-C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
each R$^{51}$ is, independently, hydrogen or forms a phthalimide moiety with the nitrogen atom to which it is attached;
each m is, independently, zero or 1; and
each n is, independently, an integer from 1 to about 6. These substituents may be synthesized by methods taught in U.S. Pat. No. 6,534,639, whose disclosure is incorporated herein by reference in its entirety.

In certain embodiments, the 2' modification is of the formula —OR$^{52}$ where R$^{52}$ is

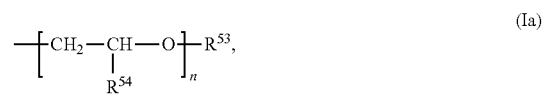

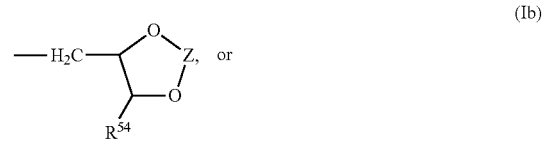

where R$^{53}$ is hydrogen, C$_1$-C$_{21}$ alkyl, C$_2$-C$_{21}$ alkenyl, C$_2$-C$_{21}$ alkynyl or —C(=O)-alkyl; R$^{54}$ is hydrogen, C$_1$-C$_{10}$ alkyl, —CH$_2$—O—R$^{55}$ or a radical of formula Ib; R$^{55}$ is hydrogen, C$_1$-C$_{22}$ alkyl, C$_3$-C$_{21}$ alkenyl, or partially or completely fluorine-substituted C$_1$-C$_{10}$ alkyl or —[(CH$_2$)$_2$—O]$_m$—R$^{56}$; R$^{56}$ is hydrogen or C$_1$-C$_{21}$ alkyl; Z is —(CH$_2$)$_p$— or —(CH$_2$—CH$_2$—O)$_q$—CH$_2$CH$_2$—, it being possible for Z in the case of —CH$_2$— to be unsubstituted or substituted by one or more identical or different substituents selected from C$_1$-C$_{10}$ alkyl, C$_5$-C$_6$ cycloalkyl and unsubstituted or C$_1$-C$_4$ alkyl-substituted phenyl; n is an integer from 1 to 12; m is an integer from 1 to 4; p is an integer from 1 to 10; and q is an integer from 1 to 4. Such substituents are described in U.S. Pat. No. 5,969,116, the disclosure of which is incorporated herein by reference in its entirety.

Some 2' substituents may be cyclic compositions of the formula:

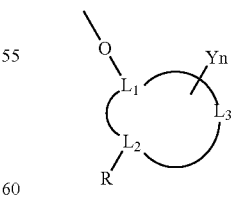

where L$_1$, L$_2$ and L$_3$ form a ring system having from about 4 to about 7 carbon atoms or having from about 3 to about 6 carbon atoms and 1 or 2 hetero atoms wherein said hetero atoms are oxygen, nitrogen or sulfur and wherein said ring system is aliphatic, unsaturated aliphatic, aromatic or heterocyclic;

R is OX, SX, N(H)X or $NX_2$;

X is H, $C_1$-$C_8$ alkyl, $C_1$-$C_8$ haloalkyl, C(=NH)N(H)Z, C(=O)N(H)Z and OC(=O)N(H)Z;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(H)X, $NX_2$, OX, halo, SX or CN;

n is 0, 1 or 2; and

Z is H or $C_1$-$C_8$ alkyl.

In certain embodiments, the ring system is phenyl, pyridyl, cyclopentyl, cyclobutyl, cyclohexyl, cycloheptyl, morpholino, piperidyl or piperazinyl with the proviso that the elected ring system is mono-, di-, or tri-substituted. In other embodiments, R is OH, SH, $OCH_3$, N(H)C(=NH)$NH_2$, N(H)C(=O)$NH_2$, $NH_2$, or OC(=O)$NH_2$. In some embodiments, $L_1$ and $L_2$ are each carbon atoms. In yet other embodiments, $L_1$ and $L_2$ are carbon atoms and the other of $L_1$ and $L_2$ is a heteroatom selected from O, S and N. These ligands may be made by methods taught by U.S. Pat. No. 6,271,358, whose disclosure is incorporated herein by reference in its entirety.

In some embodiments, the 2' position of the sugar ring can have two substituents, Y1 and Y2; provided that both Y1 and Y2 are not H and that when one of Y1 and Y2 is H and the other of Y1 and Y2 is OH, the sugar ring is other than a ribose sugar. In certain embodiments, Y1 and Y2 are each independently hydrogen; hydroxyl; halogen; $C_{2-4}$ alkenyl, $C_{2-4}$ alkynyl, or $C_{1-4}$ alkyl optionally substituted with amino, hydroxy, or 1 to 3 fluorine atoms; $C_{1-10}$ alkoxy, optionally substituted with $C_{1-3}$ alkoxy, $C_{1-3}$ thioalkoxy or 1 to 3 fluorine atoms; $C_{2-6}$ alkenyloxy; $C_{1-4}$ alkylthio; $C_{1-8}$ alkylcarbonyloxy; aryloxycarbonyl; azido; amino; $C_{1-4}$ alkylamino; di($C_{1-4}$ alkyl)amino; or $Y^3$. $Y^3$ is a conjugate molecule or a reporter molecule. These substituents are described in more detail in commonly owned U.S. patent application Ser. No. 10/444,628, the disclosure of which is incorporated by reference in its entirety. In some preferred embodiments Y1 is $C_{2-4}$ alkenyl, $C_{2-4}$ alkynyl, or $C_{1-4}$ alkyl, wherein the alkyl is unsubstituted or substituted with hydroxy, amino, $C_{1-4}$ alkoxy, $C_{1-4}$ alkylthio, or one to three fluorine atoms and Y2 is hydrogen, fluorine, hydroxy, $C_{1-10}$ alkoxy, or $C_{1-10}$ alkyl. In other preferred embodiments, Y1 is alkyl unsubstituted or substituted with hydroxy, amino, $C_{1-4}$ alkoxy, $C_{1-4}$ alkylthio, or one to three fluorine atoms, particularly where Y1 is methyl or trifluoromethyl. In yet other preferred compounds, Y2 is hydrogen or hydroxyl. These substituents are described in commonly owned U.S. patent application Ser. No. 10/444,298, the disclosure of which is incorporated herein by reference in its entirety.

Hybridization

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An oligomeric compound of the invention is believed to specifically hybridize to the target nucleic acid and interfere with its normal function to cause a loss of activity. There is preferably a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the context of the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention; "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, then the position of hydrogen bonding between the oligomer and the target nucleic acid is considered to be a complementary position. The oligomeric compound and the target nucleic acid are complementary to each other when a sufficient number of complementary positions in each molecule are occupied by nucleobases that can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomer and a target nucleic acid.

It is understood in the art that the sequence of the oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). It is preferred that the oligomeric compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Targets of the Invention

"Targeting" an oligomeric compound to a particular nucleic acid molecule, in the context of this invention, can be a multistep process. The process usually begins with the identification of a target nucleic acid whose function is to be modulated. This target nucleic acid may be, for example, a mRNA transcribed from a cellular gene whose expression is associated with a particular disorder or disease state, or a nucleic acid molecule from an infectious agent.

The targeting process usually also includes determination of at least one target region, segment, or site within the target nucleic acid for the interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using oligomeric compounds targeted to, for example, pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which preferred compounds and compositions of the invention hybridize are herein below referred to as "preferred target segments." As used herein the term "preferred target segment" is defined as at least an 8-nucleobase portion of a target region to which an active antisense oligomeric compound is targeted. While not wishing to be bound by theory, it is presently believed that these target segments represent portions of the target nucleic acid that are accessible for hybridization.

Once one or more target regions, segments or sites have been identified, oligomeric compounds are chosen which are sufficiently complementary to the target, i.e., hybridize sufficiently well and with sufficient specificity, to give the desired effect.

In accordance with an embodiment of the this invention, a series of nucleic acid duplexes comprising the antisense strand oligomeric compounds of the present invention and their respective complement sense strand compounds can be designed for a specific target or targets. The ends of the strands may be modified by the addition of one or more natural or modified nucleobases to form an overhang. The sense strand of the duplex is designed and synthesized as the complement of the antisense strand and may also contain modifications or additions to either terminus. For example, in one embodiment, both strands of the duplex would be complementary over the central nucleobases, each having overhangs at one or both termini.

For the purposes of describing an embodiment of this invention, the combination of an antisense strand and a sense strand, each of can be of a specified length, for example from 18 to 29 nucleotides long, is identified as a complementary pair of siRNA oligomers. This complementary pair of siRNA oligomers can include additional nucleotides on either of their 5' or 3' ends. Further they can include other molecules or molecular structures on their 3' or 5' ends such as a phosphate group on the 5' end. A preferred group of compounds of the invention include a phosphate group on the 5' end of the antisense strand compound. Other preferred compounds also include a phosphate group on the 5' end of the sense strand compound. An even further preferred compounds would include additional nucleotides such as a two base overhang on the 3' end.

For example, a preferred siRNA complementary pair of oligomers comprise an antisense strand oligomeric compound having the sequence CGAGAGGCG-GACGGGACCG (SEQ ID NO:1) and having a two-nucleobase overhang of deoxythymidine (dT) and its complement sense strand. These oligomers would have the following structure:

it structure wherein the first region, the antisense portion in the 5' to 3' direction, is complementary to the second region, the sense portion in the 3' to 5' direction.

In a further embodiment, the invention includes oligomer/protein compositions. Such compositions have both an oligomer component and a protein component. The oligomer component comprises at least one oligomer, either the antisense or the sense oligomer but preferably the antisense oligomer (the oligomer that is antisense to the target nucleic acid). The oligomer component can also comprise both the antisense and the sense strand oligomers. The protein component of the composition comprises at least one protein that forms a portion of the RNA-induced silencing complex, i.e., the RISC complex.

RISC is a ribonucleoprotein complex that contains an oligomer component and proteins of the Argonaute family of proteins, among others. While we do not wish to be bound by theory, the Argonaute proteins make up a highly conserved family whose members have been implicated in RNA interference and the regulation of related phenomena. Members of this family have been shown to possess the canonical PAZ and Piwi domains, thought to be a region of protein-protein interaction. Other proteins containing these domains have been shown to effect target cleavage, including the RNAse, Dicer. The Argonaute family of proteins includes, but depending on species, are not necessary limited to, eIF2C1 and eIF2C2. eIF2C2 is also known as human GERp95. While we do not wish to be bound by theory, at least the antisense oligomer strand is bound to the protein component of the RISC complex. Additional, the complex might also include the sense strand oligomer. Carmell et al, Genes and Development 2002, 16, 2733-2742.

Also while we do not wish to be bound by theory, it is further believed that the RISC complex may interact with one or more of the translation machinery components. Translation machinery components include but are not limited to proteins that effect or aid in the translation of an RNA into protein including the ribosomes or polyribosome complex. Therefore, in a further embodiment of the invention, the oligomer component of the invention is associated with a RISC protein component and further associates with the translation machinery of a cell. Such interaction with the translation machinery of the cell would include interaction with structural and enzymatic proteins of the translation machinery including but not limited to the polyribosome and ribosomal subunits.

In a further embodiment of the invention, the oligomer of the invention is associated with cellular factors such as transporters or chaperones. These cellular factors can be

```
5'     c g a g a g g c g g a c g g g a c c g T T 3' Antisense Strand (SEQ ID NO: 2)
       | | | | | | | | | | | | | | | | | |
3' T T g c t c t c c g c c t g c c c t g g c 5' Complement Strand (SEQ ID NO: 3)
```

In an additional embodiment of the invention, a single oligomer having both the antisense portion as a first region in the oligomer and the sense portion as a second region in the oligomer is selected. The first and second regions are linked together by either a nucleotide linker (a string of one or more nucleotides that are linked together in a sequence) or by a non-nucleotide linker region or by a combination of both a nucleotide and non-nucleotide structure. In each of these structures, the oligomer, when folded back on itself, would be complementary at least between the first region, the antisense portion, and the second region, the sense portion. Thus the oligomer would have a palindrome within protein, lipid or carbohydrate based and can have structural or enzymatic functions that may or may not require the complexation of one or more metal ions.

Furthermore, the oligomer of the invention itself may have one or more moieties which are bound to the oligomer which facilitate the active or passive transport, localization or compartmentalization of the oligomer. Cellular localization includes, but is not limited to, localization to within the nucleus, the nucleolus or the cytoplasm. Compartmentalization includes, but is not limited to, any directed movement of the oligomers of the invention to a cellular compartment including the nucleus, nucleolus, mitochondrion, or imbedding into a cellular membrane surrounding a compartment or the cell itself.

In a further embodiment of the invention, the oligomer of the invention is associated with cellular factors that affect gene expression, more specifically those involved in RNA modifications. These modifications include, but are not limited to posttrascriptional modifications such as methylation. Furthermore, the oligomer of the invention itself may have one or more moieties which are bound to the oligomer which facilitate the posttranscriptional modification.

The oligomeric compounds of the invention may be used in the form of single-stranded, double-stranded, circular or hairpin oligomeric compounds and may contain structural elements such as internal or terminal bulges or loops. Once introduced to a system, the oligomeric compounds of the invention may interact with or elicit the action of one or more enzymes or may interact with one or more structural proteins to effect modification of the target nucleic acid.

One non-limiting example of such an interaction is the RISC complex. Use of the RISC complex to effect cleavage of RNA targets thereby greatly enhances the efficiency of oligomer-mediated inhibition of gene expression. Similar roles have been postulated for other ribonucleases such as those in the RNase III and ribonuclease L family of enzymes.

Preferred forms of oligomeric compound of the invention include a single-stranded antisense oligomer that binds in a RISC complex, a double stranded antisense/sense pair of oligomer or a single strand oligomer that includes both an antisense portion and a sense portion. Each of these compounds or compositions is used to induce potent and specific modulation of gene function. Such specific modulation of gene function has been shown in many species by the introduction of double-stranded structures, such as double-stranded RNA (dsRNA) molecules and has been shown to induce potent and specific antisense-mediated reduction of the function of a gene or its associated gene products. This phenomenon occurs in both plants and animals and is believed to have an evolutionary connection to viral defense and transposon silencing.

The compounds and compositions of the invention are used to modulate the expression of a target nucleic acid. "Modulators" are those oligomeric compounds that decrease or increase the expression of a nucleic acid molecule encoding a target and which comprise at least an 8-nucleobase portion that is complementary to a preferred target segment. The screening method comprises the steps of contacting a preferred target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

Oligomeric Compounds

In the context of the present invention, the term "oligomeric compound" refers to a polymeric structure capable of hybridizing a region of a nucleic acid molecule. This term includes oligonucleotides, oligonucleosides, oligonucleotide analogs, oligonucleotide mimetics and combinations of these. Oligomeric compounds routinely prepared linearly but can be joined or otherwise prepared to be circular and may also include branching. Oligomeric compounds can hybridized to form double stranded compounds that can be blunt ended or may include overhangs. In general an oligomeric compound comprises a backbone of linked momeric subunits where each linked momeric subunit is directly or indirectly attached to a heterocyclic base moiety. The linkages joining the monomeric subunits, the sugar moieties or surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligomers, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligomer structure, the phosphate groups are commonly referred to as forming the internucleoside linkages of the oligomer. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions which function in a similar manner to oligonulceotides. Such non-naturally occurring oligonucleotides are often preferred the naturally occurring forms because of desirable properties such as, for example, enhanced cellular uptake, enhanced affinity for nucleic acid target and increased stability in the presence of nucleases.

In the context of this invention, the term "oligonucleotide" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetal, formacetal, thioformacetal, methylene formacetal, thioformacetal, alkeneyl, sulfamate; methyleneimino, methylenehydrazino, sulfonate, sulfonamide, amide and others having mixed N, O, S and $CH_2$ component parts.

In addition to the modifications described above, the nucleosides of the oligomeric compounds of the invention can have a variety of other modification so long as these other modifications either alone or in combination with other nucleosides enhance one or more of the desired properties described above. Thus, for nucleotides that are incorporated into oligomers of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

Altered base moieties or altered sugar moieties also include other modifications consistent with the spirit of this invention. Such oligomers are best described as being structurally distinguishable from, yet functionally interchangeable with, naturally occurring or synthetic wild type oligonucleotides. All such oligomers are comprehended by this invention so long as they function effectively to mimic the structure of a desired RNA or DNA strand. A class of representative base modifications include tricyclic cytosine analog, termed "G clamp" (Lin, et al., *J. Am. Chem. Soc.* 1998, 120, 8531). This analog makes four hydrogen bonds to a complementary guanine (G) within a helix by simultaneously recognizing the Watson-Crick and Hoogsteen faces of the targeted G. This G clamp modification when incorporated into phosphorothioate oligomers, dramatically enhances antisense potencies in cell culture. The oligomers of the invention also can include phenoxazine-substituted bases of the type disclosed by Flanagan, et al., *Nat. Biotechnol.* 1999, 17(1), 48-52.

The oligomeric compounds in accordance with this invention preferably comprise from about 8 to about 80 nucleobases (i.e. from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the oligomeric compounds of the invention are 12 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the oligomeric compounds of the invention are 15 to 30 nucleobases in length. One having ordinary skill in the art will appreciate that this embodies oligomeric compounds of 15, 16, 17, 18, 19, 20, 21, 22, 23, 24, 25, 26, 27, 28, 29, or 30 nucleobases in length.

Particularly preferred oligomeric compounds are oligomers from about 12 to about 50 nucleobases, even more preferably those comprising from about 15 to about 30 nucleobases.

General Oligomer Synthesis

Oligomerization of modified and unmodified nucleosides is performed according to literature procedures for DNA like compounds (Protocols for Oligonucleotides and Analogs, Ed. Agrawal (1993), Humana Press) and/or RNA like compounds (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

RNA oligomers can be synthesized by methods disclosed herein or purchased from various RNA synthesis companies such as for example Dharmacon Research Inc., (Lafayette, Colo.).

Irrespective of the particular protocol used, the oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

For double stranded structures of the invention, once synthesized, the complementary strands preferably are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexes are evaluated for their ability to modulate target expression. When cells reach 80% confluency, they are treated with synthetic duplexes comprising at least one oligomeric compound of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligomers, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligomers, the phosphate groups are commonly referred to as forming the internucleoside linkage or in conjunction with the sugar ring the backbone of the oligomer. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligomers containing modified e.g. non-naturally occurring internucleoside linkages. As defined in this specification, oligomers having modified internucleoside linkages include internucleoside linkages that retain a phosphorus atom and internucleoside linkages that do not have a phosphorus atom. For the purposes of this specification, and as sometimes referenced in the art, modified oligomers that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligomer backbones containing a phosphorus atom therein include, for example, phosphorothioates, chiral phosphorothioates, phosphorodithioates, phosphotri-esters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligomers having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester internucleotide linkage is represented as —O—P(=O)(OH)—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligomer backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetal and thioformacetal backbones; methylene formacetal and thioformacetal backbones; riboacetal backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., *Science,* 1991, 254, 1497-1500.

One oligonucleotide mimetic that has been reported to have excellent hybridization properties is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

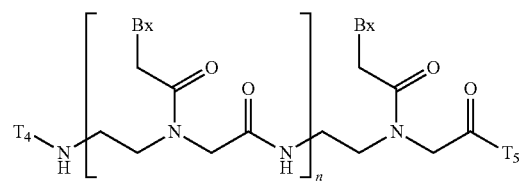

wherein

Bx is a heterocyclic base moiety;

T$_4$ is hydrogen, an amino protecting group, —C(O)R$_5$, substituted or unsubstituted C$_1$-C$_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

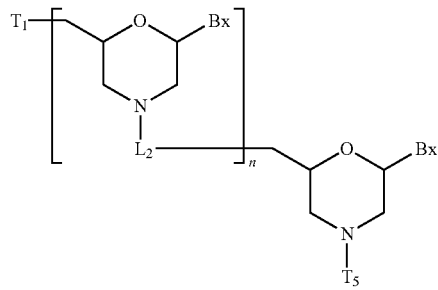

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligomers having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

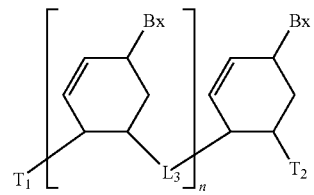

wherein each Bx is a heterocyclic base moiety;

$T_1$ is hydroxyl or a protected hydroxyl; and

T2 is hydroxyl or a protected hydroxyl.

Another preferred group of oligomeric compounds amenable to the present invention includes oligonucleotide mimetics. The term mimetic as it is applied to oligomers is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

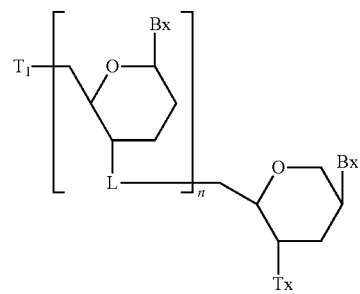

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene ($—CH_2—$)$_n$ group bridging the 2' oxygen atom and the 4' carbon atom wherein n is 1 or 2 (Singh et al., *Chem. Commun.*, 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

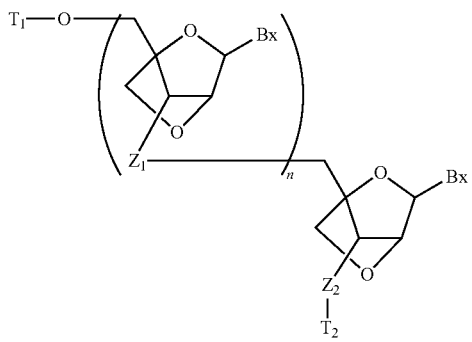

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., *J. Mol. Recognit.*, 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., *J. Am. Chem. Soc.*, 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligomers containing LNAs have been described (Wahlestedt et al., Proc. Natl. Acad. Sci. U.S.A, 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., *J. Org. Chem.*, 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

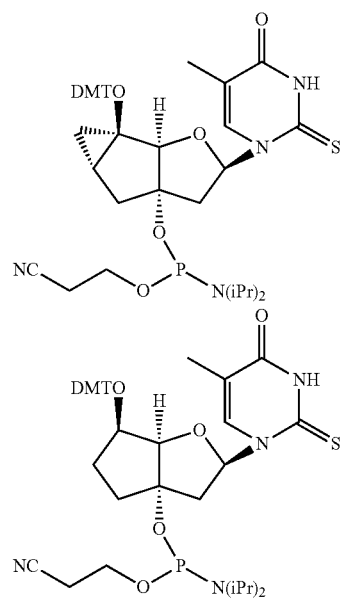

(see Steffens et al., *Helv. Chim. Acta*, 1997, 80, 2426-2439; Steffens et al., *J. Am. Chem. Soc.*, 1999, 121, 3249-3255; and Renneberg et al., *J. Am. Chem. Soc.,* 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of variables see: U.S. Pat. Nos. 5,874,553 and 6,127,346 herein incorporated by reference in their entirety) is shown below.

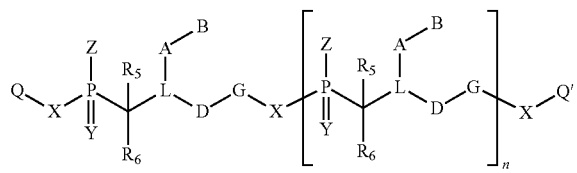

Another oligonucleotide mimetic has been reported wherein the furanosyl ring has been replaced by a cyclobutyl moiety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

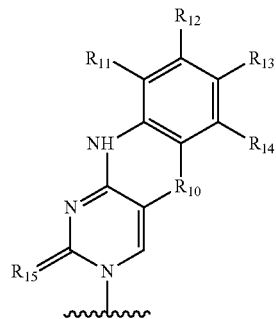

Representative cytosine analogs that make 3 hydrogen bonds with a guanosine in a second strand include 1,3-diazaphenoxazine-2-one ($R_{10}$—O, $R_{11}$-$R_{14}$=H) [Kurchavov, et al., *Nucleosides and Nucleotides,* 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155, 920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$—O, $R_{11}$=—O—($CH_2$)$_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligomers. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity make them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligomer design and to better understand the impact of these heterocyclic modifications on the biological activity, it is important to evaluate their effect on the nuclease stability of the oligomers.

Further modified polycyclic heterocyclic compounds useful as heterocycicic bases are disclosed in but not limited to, the above noted U.S. Pat. No. 3,687,808, as well as U.S. Pat. Nos. 4,845,205; 5,130,302; 5,134,066; 5,175,273; 5,367, 066; 5,432,272; 5,434,257; 5,457,187; 5,459,255; 5,484, 908; 5,502,177; 5,525,711; 5,552,540; 5,587,469; 5,594, 121; 5,596,091; 5,614,617; 5,645,985; 5,646,269; 5,750, 692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference.

Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligomer conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

3'-Endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Scheme 1

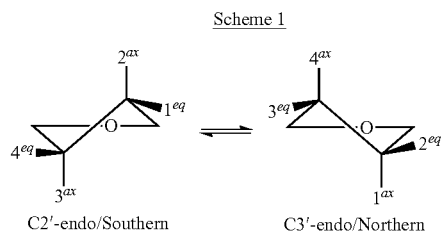

C2'-endo/Southern    C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Table I. These examples are meant to be representative and not exhaustive.

TABLE I

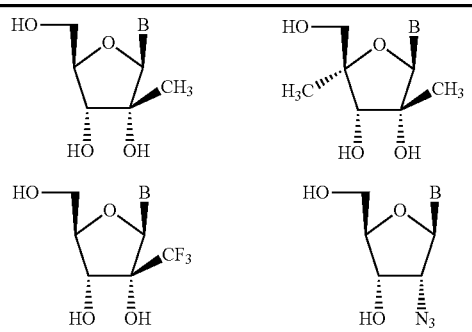

TABLE I-continued

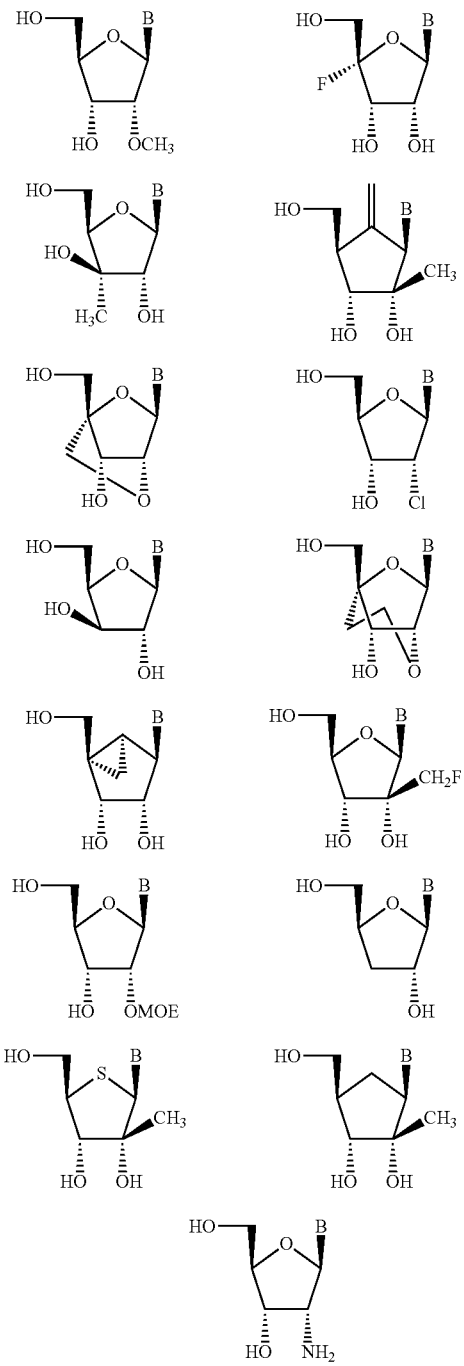

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligomers of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press, and the examples section below.) Nucleosides known to be inhibitors/substrates for RNA dependent RNA polymerases (for example HCV NS5B In one aspect, the present invention is directed to oligomers that are prepared having enhanced properties compared to native RNA against nucleic acid targets. A target is identified and an oligomer is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligomer. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and 04'-endo pucker. This is consistent with Berger, et. al., *Nucleic Acids Research,* 1998, 26, 2473-2480, who pointed out that in considering the furanose conformations which give rise to B-form duplexes consideration should also be given to a 04'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed between a target RNA and a synthetic sequence is central to therapies such as but not limited to antisense and RNA interference as these mechanisms require the binding of a synthetic oligomer strand to an RNA target strand. In the case of antisense, effective inhibition of the mRNA requires that the antisense DNA have a very high binding affinity with the mRNA. Otherwise the desired interaction between the synthetic oligomer strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligomers having the 2'-MOE modification displayed improved RNA affinity and higher nuclease resistance. Chimeric oligomers having 2'-MOE substituents in the wing nucleosides and an internal region of deoxyphosphorothioate nucleotides (also termed a gapped oligomer or gapmer) have shown effective reduction in the growth of tumors in animal models at low doses. 2'-MOE substituted oligomers have also shown outstanding promise as antisense agents in several disease states. One such MOE substituted oligomer is presently being investigated in clinical trials for the treatment of CMV retinitis.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

The term haloalkyl is defined as an alkyl containing one or more halogen atoms. In some embodiments, the alkyl is fully halogenated. For example, the haloalkyl may be trifluoromethyl. Similarly, the term haloalkoxy is defined as an alkoxy group where the alkyl group is a haloalkyl. For example, the haloalkoxy may be trifluoroalkoxy.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

Phosphotioate groups include those described in U.S. Pat. Nos. 3,687,808, 5,188,897, 5,278,302, 5,286,717, 5,405, 939, 5,453,496, and 5,587,361.

Alkylphosphoroamidate groups include those described in U.S. Pat. Nos. 5,536,821 and 5,541,306, Unless otherwise defined herein, alkoxy is defined as —O-alkyl where alkyl is as defined above.

Unless otherwise defined herein, alkylthio is defined as —S-alkyl where alkyl is as defined above.

As used herein, the terms alkyl, heteroalkyl, cycloalkyl, alkenyl, alkynyl, heterocycloalkyl, aryl, and hetaryl include moieties that are optionally substituted. Sitable substituents are well known to those skilled in the art. These substituents include $C_1$-$C_{20}$ alkyl, $C_2$-$C_{20}$ alkenyl, $C_2$-$C_{20}$ alkynyl, $C_5$-$C_{20}$ aryl, —O-alkyl, —O-alkenyl, —O-alkynyl, —O-alkylamino, —O— alkylalkoxy, —O-alkylaminoalkyl, —O-alkyl imidazole, —OH, —SH, —S-alkyl, —S-alkenyl, —S-alkynyl, —N(H)-alkyl, —N(H)-alkenyl, —N(H)-alkynyl, —N(alkyl)$_2$, —O-aryl, —S-aryl, —NH-aryl, —$ONO_2$, —O— aralkyl, —S-aralkyl, —N(H)-aralkyl, phthalimido (attached at N), halogen, amino, keto (—C(═O)—R), carboxyl (—C(═O)OH), nitro (—$NO_2$), nitroso (—N═O), cyano (—CN), trifluoromethyl (—$CF_3$), trifluoro-methoxy (—O—$CF_3$), imidazole, azido (—$N_3$), hydrazino (—N(H)—$NH_2$), aminooxy (—O—$NH_2$), isocyanato (—N═C═O), sulfoxide (—S(═O)—R), sulfone (—S(═O)$_2$—R), disulfide (—S—S—R), silyl, heterocycle, carbocycle, intercalator, reporter group, conjugate, polyamine, polyamide, polyalkylene glycol, and polyethers of the formula (—O-alkyl)$_m$, where m is 1 to about 10; wherein each R is, independently, hydrogen, a protecting group alkyl, alkenyl, or alkynyl.

The terms blockmer, 3'-hemimer, 5'-hemimer, gapmer and inverted gapmer are used in this specification to identify certain motifs or positional placement of types or segments of nucleotides in an oligomer. Depending on the number of nucleotide or nucleoside subunits and their position in the oligomer, one or more than one of these terms might apply to a particular construction and could be used for identification purposes. A blockmer has at least one block or segment of at least two consecutively located nucleotide or nucleoside subunits of a first type positioned adjacent to at least one nucleotide or nucleoside of a second type. Thus for instances if the nucleotides or nucleosides of the first type are represented by "X" and those of the second type are represented by "Y" and if " . . . " represent nucleotides or nucleosides other that the X or Y type nucleotides or the absence of any nucleotides then the following structures . . . XXY . . . ; . . . XXYXX . . . ; . . . XXY-XXY . . . ; . . . XXYXXYXX . . . on so on for higher homologs are possible where each X containing segment includes two members and each Y containing segment includes only one member. If each X containing segment includes two members and each Y subunit also includes two members other representational blockmers include . . . XXYY . . . ; . . . XXYYXX . . . ; . . . XXYYX-XYY . . . ; . . . XXYYXXYYXX . . . and so on for high homologs. These can be extended to other representative structures having more X and/or Y members in the blocks or segments, as for instances the structures YXXXXYYYXXXXY; YYXXXYYXXXXYY; and YYYYXXXXYYYYXXXX.

If a block or segment of the first type of nucleotides or nucleoside resides at the 5' or the 3' terminus and all of the remaining nucleotides or nucleosides of the oligomer are of the second type, then that blockmer is also a hemimer. Using the same X and Y representation and selecting five members for each segment and basing the hemimer designation on the X members then the representations XXXXXYYYYY and YYYYYXXXX represent, respectively, 5' and 3' hemimers.

In gapmers, a block or segment of one type of nucleotides or nucleosides is interspaced between first and second blocks of the second type. As before if the designation is based on the X members then XXXXXYYYYXXXX represents a gapmer and YYYYXXXXYYYY represents an invertered gapmer.

Screening, Target Validation and Drug Discovery

For use in screening and target validation, the compounds and compositions of the invention are used to modulate the expression of a selected protein. "Modulators" are those oligomeric compounds and compositions that decrease or increase the expression of a nucleic acid molecule encoding a protein and which comprise at least an 8-nucleobase portion which is complementary to a preferred target segment. The screening method comprises the steps of contacting a preferred target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The conduction such screening and target validation studies, oligomeric compounds of invention can be used combined with their respective complementary strand oligomeric compound to form stabilized double-stranded (duplexed) oligomers. Double stranded oligomer moieties have been shown to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200; Nishikura et al., *Cell* (2001), 107, 415-416; and Bass et al., *Cell* (2000), 101, 235-238.) For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

For use in drug discovery and target validation, oligomeric compounds of the present invention are used to elucidate relationships that exist between proteins and a disease state, phenotype, or condition. These methods include detecting or modulating a target peptide comprising contacting a sample, tissue, cell, or organism with the oligomeric compounds and compositions of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a disease or disorder.

Kits, Research Reagents, Diagnostics, and Therapeutics

The oligomeric compounds and compositions of the present invention can additionally be utilized for diagnostics, therapeutics, prophylaxis and as research reagents and kits. Such uses allows for those of ordinary skill to elucidate the function of particular genes or to distinguish between functions of various members of a biological pathway.

For use in kits and diagnostics, the oligomeric compounds and compositions of the present invention, either alone or in combination with other compounds or therapeutics, can be used as tools in differential and/or combinatorial analyses to elucidate expression patterns of a portion or the entire complement of genes expressed within cells and tissues.

As one non-limiting example, expression patterns within cells or tissues treated with one or more compounds or compositions of the invention are compared to control cells or tissues not treated with the compounds or compositions and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compounds and compositions of the invention are useful for research and diagnostics, because these compounds and compositions hybridize to nucleic acids encoding proteins. Hybridization of the compounds and compositions of the invention with a nucleic acid can be detected by means known in the art. Such means may include conjugation of an enzyme to the compound or composition, radiolabelling or any other suitable detection means. Kits using such detection means for detecting the level of selected proteins in a sample may also be prepared.

The specificity and sensitivity of compounds and compositions can also be harnessed by those of skill in the art for therapeutic uses. Antisense oligomeric compounds have been employed as therapeutic moieties in the treatment of disease states in animals, including humans. Antisense oligomer drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, preferably a human, suspected of having a disease or disorder that can be treated by modulating the expression of a selected protein is treated by administering the compounds and compositions. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In one embodiment, the activity or expression of a protein in an animal is inhibited by about 10%. Preferably, the activity or expression of a protein in an animal is inhibited by about 30%. More preferably, the activity or expression of a protein in an animal is inhibited by 50% or more.

For example, the reduction of the expression of a protein may be measured in serum, adipose tissue, liver or any other body fluid, tissue or organ of the animal. Preferably, the cells contained within the fluids, tissues or organs being analyzed contain a nucleic acid molecule encoding a protein and/or the protein itself.

The compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

Formulations

The compounds and compositions of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the invention are prepared as SATE [(S-acetyl-2-thioethyl)phosphate]derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds and compositions of the invention: i.e., salts that retain the desired biological activity of the parent compound and do not impart undesired toxicological effects thereto. For oligomers, preferred examples of pharmaceutically acceptable salts and their uses are further described in U.S. Pat. No. 6,287,860, which is incorporated herein in its entirety.

The present invention also includes pharmaceutical compositions and formulations that include the compounds and compositions of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compounds and compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligomers of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, compounds and compositions of the invention may be encapsulated within liposomes or may form complexes thereto, in particular to cationic liposomes. Alternatively, they may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligomers of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Compounds and compositions of the invention may be delivered orally, in granular form including sprayed dried particles, or complexed to form micro or nanoparticles. Complexing agents and their uses are further described in U.S. Pat. No. 6,287,860, which is incorporated herein in its entirety. Certain oral formulations for oligomers and their preparation are described in detail in U.S. application Ser. No. 09/108,673 (filed Jul. 1, 1998), Ser. No. 09/315,298 (filed May 20, 1999) and Ser. No. 10/071, 822, filed Feb. 8, 2002, each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more of the compounds and compositions of the invention and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the oligomeric compounds of the invention, such chemotherapeutic agents may be used individually (e.g., 5-FU and oligomer), sequentially (e.g., 5-FU and oligomer for a period of time followed by MTX and oligomer), or in combination with one or more other such chemotherapeutic agents (e.g., 5-FU, MTX and oligomer, or 5-FU, radiotherapy and oligomer). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of compounds and compositions of the invention and other drugs are also within the scope of this invention. Two or more combined compounds such as two oligomeric compounds or one oligomeric compound combined with further compounds may be used together or sequentially.

In another related embodiment, compositions of the invention may contain one or more of the compounds and compositions of the invention targeted to a first nucleic acid and one or more additional compounds such as antisense oligomeric compounds targeted to a second nucleic acid target. Numerous examples of antisense oligomeric compounds are known in the art. Alternatively, compositions of the invention may contain two or more oligomeric compounds and compositions targeted to different regions of the same nucleic acid target. Two or more combined compounds may be used together or sequentially Dosing The formulation of therapeutic compounds and compositions of the invention and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

The entire disclosure of each patent, patent application, and publication cited or described in this document is hereby incorporated by reference.

EXAMPLE 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-N$^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N$^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N$^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'4)-[2-phthalimidoxy)ethyl]-5'-t-butyldiphenylsilyl-5-methyluridine, 5'-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

EXAMPLE 2

Oligonucleotide and Oligonucleoside Synthesis

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

EXAMPLE 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2"-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5"-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5"-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand*, 1990, 44, 639-641; Reddy, M. P., et al., *Tetrahedrom Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

EXAMPLE 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]—[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

EXAMPLE 5

Synthesis of 2'-Deoxy-2'-fluoro Modified Oligonucleotides

2'-Deoxy-2'-fluoro modified oligonucleotides may be prepared by methods taught in U.S. Pat. No. 6,531,584.

EXAMPLE 6

Synthesis of 2'-Deoxy-2'-O-alkyl Modified Oligonucleotides

2'-Deoxy-2'-O-alkyl modified oligonucleotides may be prepared by methods taught in U.S. Pat. No. 6,531,584.

EXAMPLE 7

Synthesis of 2'-O-[2(2-N,N-dimethylaminoethoxy) ethyl]-5-methyl Uridine

2'-O-[2(2-N,N-dimethylaminoethoxy)ethyl]-5-methyl uridine may be prepared by methods taught in U.S. Pat. No. 6,043,352.

EXAMPLE 8

Synthesis of 5'-O-Dimethoxytrityl-2'-O-methyl-3'-O—(N,N-diisopropylamino-O-(3-cyano ethylphosphine)-N-benzoyladenosine 5'-O-Dimethoxytrityl-2'-O-methyl-3'-O—(N,N-diisopropylamino-O-.beta.-cyano ethylphosphine)-N-benzoyladenosine may be prepared by methods taught in U.S. Pat. No. 6,005,094.

EXAMPLE 9

Synthesis of 5'-O-Dimethoxytrityl-2'-O-Methylthiomethyl-Nucleotides

5'-O-Dimethoxytrityl-2'-O-methylthiomethyl-nucleotides may be prepared by methods taught in U.S. Pat. No. 6,239,272.

EXAMPLE 10

Synthesis of 2'-Deoxy-2'-(vinyloxy) Modified Oligonucleotides

2'-Deoxy-2'-(vinyloxy) modified oligonucleotides may be prepared by methods taught in U.S. Pat. No. 5,859,221.

EXAMPLE 11

Synthesis of 2'-Deoxy-2'-(methylthio), (methylsulfinyl) and (methylsulfonyl) Modified Oligonucleotides 2'-Deoxy-2'-(methylthio), (methylsulfinyl) and (methylsulfonyl) modified oligonucleotides may be prepared by methods taught in U.S. Pat. No. 5,859,221.

EXAMPLE 12

Synthesis of Oligonucleotides Bearing 2'-OCH$_2$COOEt Substituents

2'-OCH$_2$COOEt modified oligonucleotides may be prepared by methods taught in U.S. Pat. No. 5,792,847.

EXAMPLE 13

Synthesis of 9-(2-(O-2-Propynyloxy)-β-D-ribofuranosyl) Adenine 9-(2-(O-2-Propynyloxy)-β-D-ribofuranosyl) adenine may be prepared by methods taught in U.S. Pat. No. 5,514,786.

EXAMPLE 14

Synthesis of 3'-O—(N-Allyloxycarbonyl-6-aminohexyl)-5'-O-dimethoxytrityl-uridine 3'-O—(N-Allyloxycarbonyl-6-aminohexyl)-5'-O-dimethoxytrityl-uridine may be prepared by methods taught in U.S. Pat. No. 6,111,085.

EXAMPLE 15

Synthesis of 2'-O—(N-phthalimido) prop-3-yl adenosine

2'-O—(N-phthalimido) prop-3-yl adenosine may be prepared by methods taught in U.S. Pat. No. 5,872,232.

EXAMPLE 16

Synthesis of 2'-O-(2-Phthalimido-N-hydroxyethyl)-3',5'-O-(1,1,3,3-tetraisopropyldisiloxane-1,3-diyl) adenosine 2'-O-(2-Phthalimido-N-hydroxyethyl)-3',5'-O-(1,1,3,3-tetraisopropyldisiloxane-1,3-diyl)adenosine may be prepared by methods taught in U.S. Pat. No. 6,172,209.

EXAMPLE 17

Synthesis of 5'-O-Dimethoxytrityl-2'-O-(carbonylaminohexyl aminocarbonyloxy cholesteryl)-N₄-benzolyl chloride 5'-O-Dimethoxytrityl-2'-O-(carbonylaminohexyl aminocarbonyloxy cholesteryl)-N4-benzolyl chloride may be prepared by methods taught in U.S. Pat. No. 6,166,188.

EXAMPLE 18

Synthesis of 5'-O-[(2,2-dimethyl-1,1-diphenyl-1-silapropoxy)methyl]-2'-O—((N,N-dimethylaminoethyleneamino)carbonylmethylene)adenosine 5'-O-[(2,2-dimethyl-1,1-diphenyl-1-silapropoxy)methyl]-2'-O—((N,N-dimethylaminoethyleneamino)carbonylmethylene)adenosine may be prepared by methods taught in U.S. Pat. No. 6,147,200.

EXAMPLE 19

Synthesis of 2'-O-(Propylsulfonic acid) Sodium Salt-N-3-(Benzyloxy) Methyl-5-Methyluridine 2'-O-(Propylsulfonic acid) sodium salt-N-3-(benzyloxy) methyl-5-methyluridine may be prepared by methods taught in U.S. Pat. No. 6,277,982.

EXAMPLE 20

Synthesis of

2'-O—H₂C—[epoxide structure]

Modified Oligonucleotides

These oligonucleotides may be prepared by methods taught in U.S. Pat. No. 5,969,116.

EXAMPLE 21

Synthesis of 5'-Dimethoxytrityl-2'-O-(trans-2-methoxycyclohexyl)-5-methyl Uridine 5'-Dimethoxytrityl-2'-O-(trans-2-methoxycyclohexyl)-5-methyl uridine may be prepared by methods taught in U.S. Pat. No. 6,277,982.

EXAMPLE 22

Synthesis of 2'-OH, 2'-Me Modified Compounds

[Structure of adenosine derivative with 2'-Me, 2'-OH]

The above compound was prepared following the methods described in *J. Med. Chem.* 41: 1708 (1998).

EXAMPLE 23

4-Amino-7-(2-C-methyl-β-D-arabinofuranosyl)-7H-pyrrolo[2,3-d]pyrimidine

[Structure of pyrrolopyrimidine nucleoside with 2'-Me, 2'-OH]

To CrO₃ (1.57 g, 1.57 mmol) in dichloromethane (DCM) (10 mL) at 0° C. was added acetic anhydride (145 mg, 1.41 mmol) and then pyridine (245 mg, 3.10 mmol). The mixture was stirred for 15 min, then a solution of 7-[3,5-O-[1,1,3,3-tetrakis(1-methylethyl)-1,3-disiloxanediyl]-β-D-ribofuranosyl]-7H-pyrrolo[2,3-c]pyrimidin-4-amine [for preparation, see *J. Am. Chem. Soc.* 105: 4059 (1983)] (508 mg, 1.00 mmol) in DCM (3 mL) was added. The resulting solution was stirred for 2 h and then poured into ethyl acetate (10 mL), and subsequently filtered through silica gel using ethyl acetate as the eluent. The combined filtrates were evaporated in vacuo, taken up in diethyl ether/THF (1:1) (20 mL), cooled to −78° C. and methylmagnesium bromide (3M, in THF) (3.30 mL, 10 mmol) was added dropwise. The mixture was stirred at −78° C. for 10 min, then allowed to come to room temperature (rt) and quenched by addition of saturated aqueous ammonium chloride (10 mL) and extracted with DCM (20 mL). The organic phase was evaporated in vacuo and the crude product purified on silica gel using 5% methanol in dichloromethane as eluent. Fractions containing the product were pooled and evaporated in vacuo. The resulting oil was taken up in THF (5 mL) and tetrabutylammonium fluoride (TBAF) on silica (1.1 mmol/g on silica) (156 mg) was added. The mixture was stirred at rt for 30 min, filtered, and evaporated in vacuo. The crude product was purified on silica gel using 10% methanol in dichloromethane as eluent. Fractions containing the product were pooled and evaporated in vacuo to give the desired compound (49 mg) as a colorless solid.

$^1$H NMR (DMSO-$d_6$): δ 1.08 (s, 3H), 3.67 (m, 2H), 3.74 (m, 1H), 3.83 (m, 1H), 5.19 (m, 1H), 5.23 (m, 1H), 5.48 (m, 1H), 6.08 (1H, s), 6.50 (m, 1H), 6.93 (bs, 2H), 7.33 (m, 1H), 8.02 (s, 1H).

EXAMPLE 24

Design and Screening of Duplexed Oligomeric Compounds Targeting a Target

In accordance with the present invention, a series of nucleic acid duplexes comprising the antisense oligomeric compounds of the present invention and their complements can be designed to target a target. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO:1) and having a two-nucleobase overhang of deoxythymidine (dT) would have the following structure:

```
5'      c g a g a g g c g g a c g g g a c c g T T 3'  Antisense Strand (SEQ ID NO: 2)
        | | | | | | | | | | | | | | | | | | |
3' T T  g c t c t c c g c c t g c c c t g g c      5'  Complement Strand (SEQ ID NO: 3)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense oligomeric compounds are evaluated for their ability to modulate a target expression.

When cells reached 80% confluency, they are treated with duplexed antisense oligomeric compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense oligomeric compound at a final concentration of 200 nM. After 5 hours of treatment, the medium is replaced with fresh medium. Cells are harvested 16 hours after treatment, at which time RNA is isolated and target reduction measured by RT-PCR.

EXAMPLE 25

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH₄OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

EXAMPLE 26

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH₄OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

EXAMPLE 27

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the oligomeric compounds utilizing electrospray-mass spectroscopy. All assay test plates were diluted from the master plate using single and multi-channel robotic pipettors. Plates were judged to be acceptable if at least 85% of the oligomeric compounds on the plate were at least 85% full length.

EXAMPLE 28

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR. T-24 cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Oligomeric Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 4) which is targeted to human H-ras, or ISIS 18078, (GTGCGCGCGAGCCCGAAATC, SEQ ID NO: 5) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 6, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

EXAMPLE 29

Analysis of Oligonucleotide Inhibition of a Target Expression

Modulation of a target expression can be assayed in a variety of ways known in the art. For example, a target mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

EXAMPLE 30

Design of Phenotypic Assays and In Vivo Studies for the Use of a Target Inhibitors Phenotypic Assays Once a target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.;

BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or a target inhibitor. Furthermore, to prevent the doctors from being biased in treatments, they are not informed as to whether the medication they are administering is a a target inhibitor or a placebo. Using this randomization approach, each volunteer has the same chance of being given either the new treatment or the placebo.

Volunteers receive either the a target inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding a target or a target protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/ great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and a target inhibitor treatment. In general, the volunteers treated with placebo have little or no response to treatment, whereas the volunteers treated with the target inhibitor show positive trends in their disease state or condition index at the conclusion of the study.

EXAMPLE 31

RNA Isolation

Poly(A)+mRNA Isolation

Poly(A)+mRNA was isolated according to Miura et al., (*Clin. Chem.*, 1996, 42, 1758-1764). Other methods for poly(A)+mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

EXAMPLE 32

Real-Time Quantitative PCR Analysis of a Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers are designed to hybridize to a human a target sequence, using published sequence information.

EXAMPLE 33

Northern Blot Analysis of a Target mRNA Levels

Eighteen hours after treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Cross-linker 2400 (Stratagene, Inc, La Jolla, Calif.) and then probed using QUICKHYB™ hybridization solution (Stratagene, La Jolla, Calif.) using manufacturer's recommendations for stringent conditions.

To detect human a target, a human a target specific primer probe set is prepared by PCR To normalize for variations in loading and transfer efficiency membranes are stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™

Software V3.3 (Molecular Dynamics, Sunnyvale, Calif.). Data was normalized to GAPDH levels in untreated controls.

EXAMPLE 34

Inhibition of Human a Target Expression by Oligonucleotides

In accordance with the present invention, a series of oligomeric compounds are designed to target different regions of the human target RNA. The oligomeric compounds are analyzed for their effect on human target mRNA levels by quantitative real-time PCR as described in other examples herein. Data are averages from three experiments. The target regions to which these preferred sequences are complementary are herein referred to as "preferred target segments" and are therefore preferred for targeting by oligomeric compounds of the present invention. The sequences represent the reverse complement of the preferred antisense oligomeric compounds.

As these "preferred target segments" have been found by experimentation to be open to, and accessible for, hybridization with the antisense oligomeric compounds of the present invention, one of skill in the art will recognize or be able to ascertain, using no more than routine experimentation, further embodiments of the invention that encompass other oligomeric compounds that specifically hybridize to these preferred target segments and consequently inhibit the expression of a target.

According to the present invention, antisense oligomeric compounds include antisense oligomeric compounds, antisense oligonucleotides, ribozymes, external guide sequence (EGS) oligonucleotides, alternate splicers, primers, probes, and other short oligomeric compounds that hybridize to at least a portion of the target nucleic acid.

EXAMPLE 35

Western Blot Analysis of a Target Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

EXAMPLE 36

Blockmer Walk of 5 2'-O-Methy Modified Nucleosides in the Antisense Strand of siRNA's Assayed for PTEN mRNA Levels Against Untreated Control The antisense (AS) strands listed below having SEQ ID NO: 8 were individually duplexed with the sense (S) strand having SEQ ID NO: 7 and the activity was measured to determine the relative positional effect of the 5 modifications.

| SEQ ID NO:/ISIS NO | Sequence |
|---|---|
| 7/271790(S) | 5'-CAAAUCCAGAGGCUAGCAG-dTdT-3' |
| 8/271071(AS) | 3'-dTdT-GUUUAGGUCUCCGA<u>UCGUC</u>-5' |
| 8/271072(AS) | 3'-dTdT-GUUUAGGUCUCCG<u>AUCGU</u>C-5' |
| 8/271073(AS) | 3'-dTdT-GUUUAGGUCUCC<u>GAUCG</u>UC-5' |
| 8/271074(AS) | 3'-dTdT-GUUUAGGUCUC<u>CGAUC</u>GUC-5' |
| 8/271075(AS) | 3'-dTdT-GUUUAGGUCU<u>CCGAU</u>CGUC-5' |

Underlined nucleosides are 2'-O-methyl modified nucleosides, dT's are deoxy thymidines, all other nucleosides are ribonucleosides and all internucleoside linkages are phosphodiester.

The siRNA's having 5, 2'-O-methyl groups at least 2 positions removed from the 5'-end of the antisense strand reduced PTEN mRNA levels to from 25 to 35% of untreated control. The remaining 2 constructs increased PTEN mRNA levels above untreated control.

EXAMPLE 37

Solid Block of 2'-O-Methyl Modified Nucleosides in the Antisense Strand of siRNA's Assayed for PTEN mRNA Levels Against Untreated Control The antisense strands listed below having SEQ ID NO:9 were individually duplexed with the sense strand having SEQ ID NO:7 and the activity was measured to determine the relative effect of adding either 9 or 14, 2'-O-methyl modified nucleosides at the 3'-end of the resulting siRNA's.

| SEQ ID NO:/ISIS NO | Sequence |
|---|---|
| 7/271790(S) | 5'-CAAAUCCAGAGGCUAGCAG-dTdT-3' |
| 9/271079(AS) | 3'-<u>UUGUUUAGG</u>UCUCCGAUCGUC-5' |
| 9/271081(AS) | 3'-<u>UUGUUUAGGUCUCC</u>GAUCGUC-5' |

Underlined nucleosides are 2'-O-methyl modified nucleosides, dT's are deoxy thymidines, all other nucleosides are ribonucleosides and all internucleoside linkages are phosphodiester.

| SEQ ID NO: | Sequence (5'-3') |
|---|---|
| 9 | CUGCUAGCCUCUGGAUUUGUU |

The siRNA having 9, 2'-O-methyl nucleosides reduced PTEN mRNA levels to about 40% of untreated control whereas the construct having 14, 2'-O-methyl nucleosides only reduced PTEN mRNA levels to about 98% of control.

EXAMPLE 38

2'-O-Methy Blockmers (siRNA Vs asRNA)

A series of blockmers were prepared as duplexed siRNA's and also as single strand asRNA's. The antisense strands were identical for the siRNA's and the asRNA's.

| SEQ ID NO:/ISIS NO | | Sequence 5'-3' | |
|---|---|---|---|
| 10/308746 | (S) | 5'-AAGUAAGGACCAGAGACAAA-3' | (PO) |
| 11/303912 | (AS) | 3'-UUCAUUCCUGGUCUCUGUUU-P 5' | (PS) |
| 11/316449 | (AS) | 3'-UUCAUUCCUGGUCUCUGUUU-P 5' | (PS) |
| 11/335223 | (AS) | 3'-UUCAUUCCUGGUCUCUGUUU-P 5' | (PS) |
| 11/335224 | (AS) | 3'-UUCAUUCCUGGUCUCUGUUU-P 5' | (PS) |
| 11/335225 | (AS) | 3'-UUCAUUCCUGGUCUCUGUUU-P 5' | (PS) |
| 11/335226 | (AS) | 3'-UUCAUUCCUGGUCUCUGUUU-P 5' | (PS) |
| 11/335227 | (AS) | 3'-UUCAUUCCUGGUCUCUGUUU-P 5' | (PS) |
| 11/335228 | (AS) | 3'-UUCAUUCCUGGUCUCUGUUU-P 5' | (PS) |

Underlined nucleosides are 2'-O-methyl modified nucleosides, all other nucleosides are ribonucleosides and all internucleoside linkages for the AS strands are phosphorothioate and the internucleoside linkages for the S strand are phosphodiester.

| SEQ ID NO: | Sequence (5'-3') |
|---|---|
| 10 | AAGUAAGGACCAGAGACAAA |
| 11 | UUUGUCUCUGGUCCUUACUU |

The constructs were assayed for activity for measuring the levels of PTEN mRNA in T24 cells against untreated control levels. All of the asRNA's and siRNA's showed activity with the asRNA's having the best activity in each case. A clear dose response was seen for all the siRNA constructs (20, 40, 80 and 150 nm doses). There was a good dose response for the asRNA's for 50, 100 and 200 nm doses. In general the siRNA's were more active in this system at lower doses than the asRNA's and at the 150 nm dose was able to reduce PTEN mRNA levels to from 15 to 40% of untreated control. The unmodified siRNA 303912 reduced PTEN mRNA levels to about 19% of the untreated control.

EXAMPLE 39

3'-Hemimer 2'-O-Methyl siRNA Constructs

Blunt and overhanging siRNA constructs were prepared having a block of 5, 2'-O-methyl nucleosides at the 3'-terminus.

| SEQ ID NO:/ISIS NO | Sequence (overhangs) |
|---|---|
| 7/271790 (S) | 5'-CAAAUCCAGAGGCUAGCAG-dTdT-3' |
| 9/xxxxxx (AS) | 3'-UUGUUUAGGUCUCCGAUCGUC-5' |

| SEQ ID NO:/ISIS NO | Sequence (blunt) |
|---|---|
| 12/xxxxx(S) | 5'-GUCAAAUCCAGAGGCUAGCAG-3' |
| 13/xxxxxx (AS) | 3'-CAGUUUAGGUCUCCGAUCGUC-5' |

Underlined nucleosides are 2'-O-methyl modified nucleosides, all other nucleosides are ribonucleosides and all internucleoside linkages for the AS strands are phosphorothioate and the internucleoside linkages for the S strand are phosphodiester.

| SEQ ID NO: | Sequence (5'-3') |
|---|---|
| 12 | GUCAAAUCCAGAGGCUAGCAG |
| 13 | CUGCUAGCCUCUGGAUUUGAC |

The construct having overhangs was able to reduce PTEN mRNA levels to about 36% of untreated control whereas the blunt ended construct was able to reduce the PTEN mRNA levels to about 27% of untreated control.

EXAMPLE 40 siRNA Hemimer Constructs

Three siRNA hemimer constructs were prepared and examined in a PTEN assay. The hemimer constructs had 7, 2'-O-methyl nucleosides at the 3'-end. The hemimer was put in the sense strand only, the antisense strand only and in both strands to compare the effects.

| SEQ ID NO:/ISIS NO | Constructs (overhangs) |
|---|---|
| 14/271068 (S) | 5'-CAAAUCCAGAGGCUAGCAGUU-3' |
| 9/ (AS) | 3'-UUGUUUAGGUCUCCGAUCGUC-5' |
| 14/271068 (S) | 5'-CAAAUCCAGAGGCUAGCAGUU-3' |
| 9/ (AS) | 3'-UUGUUUAGGUCUCCGAUCGUC-5' |
| 14/ (S) | 5'-CAAAUCCAGAGGCUAGCAGUU-3' |
| 9/ (AS) | 3'-UUGUUUAGGUCUCCGAUCGUC-5' |

Underlined nucleosides are 2'-O-methyl modified nucleosides, all other nucleosides are ribonucleosides and all internucleoside linkages for the AS strands are phosphorothioate and the internucleoside linkages for the S strand are phosphodiester.

| SEQ ID NO: | Sequence (5'-3') |
|---|---|
| 14 | CAAAUCCAGAGGCUAGCAGUU |

The construct having the 7, 2'-O-methyl nucleosides only in the antisense strand reduced PTEN mRNA levels to about 23% of untreated control. The construct having the 7, 2'-O-methyl nucleosides in both strands reduced the PTEN mRNA levels to about 25% of untreated control. When the 7, 2'-O-methyl nucleosides were only in the sense strand PTEN mRNA levels were reduced to about 31% of untreated control.

EXAMPLE 41 siRNA Vs asRNA Hemimers

Four hemimers were prepared and assayed as the asRNA's and also as the siRNA's in a PTEN assay. The unmodified sequence was also tested as the asRNA and as the siRNA.

| SEQ ID NO:/ ISIS NO | Constructs (overhangs) |
|---|---|
| 10/308746 (S) | 5'-AAGUAAGGACCAGAGACAAA-3' |
| 11/303912 (AS) | 3'-UUCAUUCCUGGUCUCUGUUU-P 5' |
| 11/316449 (AS) | 3'-<u>UUC</u>AUUCCUGGUCUCUGUUU-P 5' |
| 11/319013 (AS) | 3'-<u>UUCAU</u>UCCUGGUCUCUGUUU-P 5' |
| 11/319014 (AS) | 3'-<u>UUCAUUC</u>CUGGUCUCUGUUU-P 5' |
| 11/319015 (AS) | 3'-<u>UUCAUUCC</u>UGGUCUCUGUUU-P 5' |

Underlined nucleosides are 2'-O-methyl modified nucleosides, all other nucleosides are ribonucleosides and all internucleoside linkages for the AS strands are phosphorothioate and the internucleoside linkages for the S strand are phosphodiester.

| Construct | siRNA (% mRNA) | asRNA (% mRNA) |
|---|---|---|
| 11/303912 | 21 | 32 |
| 11/316449 | 17 | 26 |
| 11/319013 | 34 | 32 |
| 11/319014 | 54 | 42 |
| 11/319015 | 51 | 42 |

Percent mRNA is relative to untreated control in PTEN assay.

EXAMPLE 42

Representative siRNA's Prepared Having 2'O-Me Gapmers

The following antisense strands of siRNA's were hybridized to the complementary full phosphodiester sense strand. Bolded monomers are 2'-OCH₃ (also referred to as 2'-OMe) containing monomers. Underlined monomers have PS linkages. Monomers without underlines have PO linkages.

| SEQ ID NO/ISIS NO | | |
|---|---|---|
| 15/300852 | 5'-OH-CUG CUA GCC UCU GGA UUU GA | (OMe/PO) |
| 15/300853 | 5'-P-CUG CUA GCC UCU GGA UUU GA | (OMe/PO) |
| 15/300854 | 5'-OH-CUG CUA GCC UCU GGA UUU GA | (OMe/PO) |
| 15/300855 | 5'-P-C<u>UG</u> CUA GCC UCU GGA UUU GA | (OMe/PO/<u>PS</u>) |
| 16/300856 | 5' OH-CUA GCC UCU GGA UUU GA | (OMe/PO/<u>PS</u>) |
| 15/300858 | 5'-OH-C<u>UG</u> CUA GCC UCU GGA UUU GA | (OMe/<u>PS</u>) |
| 15/300859 | 5'-P-CUG CUA GCC UCU GGA UUU GA | (OMe/<u>PS</u>) |
| 16/300860 | 5'-OH-CUA GCC UCU GGA UUU GA | (OMe/<u>PS</u>) |
| 17/303913 | 5'-OH-GUC UCU GGU CCU UAC UU | (OMe/<u>PS</u>) |
| 18/303915 | 5'-OH-UUU UGU CUC UGG UCC UU | (OMe/<u>PS</u>) |
| 19/303917 | 5'-OH-CUG GUC CUU ACU UCC CC | (OMe/<u>PS</u>) |
| 20/308743 | 5' P-UUU GUC UCU GGU CCU UAC UU | (OMe/<u>PS</u>) |
| 21/308744 | 5'-P-UCU CUG GUC CUU ACU UCC CC | (OMe/<u>PS</u>) |
| 22/328795 | 5'-P-UUU GUC UCU GGU CCU UAC UU | (OMe/<u>PS</u>) |

EXAMPLE 43

Representative siRNA's Prepared Having 2'-O-Methyl Modified Nucleosides

The following antisense strands of siRNA's were hybridized to the complementary full phosphodiester sense strand. Where the antisense strand has a TT 3'-terminus the corresponding sense strand also has a 3'-TT (deoxyT's)

| SEQ ID NO./ISIS NO. | | |
|---|---|---|
| 23/271065 | CUG CUA GCC UCU GGA UUU GTT | PO |
| 24/271067 | CUG CUA GCC UCU GGA UUU GUU | PO |
| 25/271069 | CUG CUA GCC UCU GGA UUU GUT | PO |
| 23/271071 | CUG CUA GCC UCU GGA UUU GTT | PO |
| 23/271072 | CUG CUA GCC UCU GGA UUU GTT | PO |
| 23/271073 | CUG CUA GCC UCU GGA UUU GTT | PO |
| 23/271074 | CUG CUA GCC UCU GGA UUU GTT | PO |
| 23/271075 | CUG CUA GCC UCU GGA UUU GTT | PO |
| 23/271076 | CUG CUA GCC UCU GGA UUU GTT | PO |
| 23/271077 | CUG CUA GCC UCU GGA UUU GTT | PO |
| 23/271078 | CUG CUA GCC UCU GGA UUU GTT | PO |
| 24/271079 | CUG CUA GCC UCU GGA UUU GUU | PO |

| SEQ ID NO./ ISIS NO. | |
|---|---|
| 25/271081 | CUG CUA GCC TCT GGA TTT GUU PO |
| 26/271082 | CUG CUA GCC UCU GGA UUU GAC PO/PS |
| 25/271083 | CUG CUA GCC UCU GGA UUU GUU PO/PS |
| 23/271084 | CUG CUA GCC UCU GGA UUU GTT PO |
| 23/283547 | CUG CUA GCC UCU GGA UUU GTT PO |
| 23/293999 | CUG CUA GCC UCU GGA UUU GTT PO |
| 23/294000 | CUG CUA GCC UCU GGA UUU GTT PO |
| 23/290223 | CUG CUA GCC UCU GGA UUU GTT PO |

EXAMPLE 44

Representative siRNA's Prepared Having 2'-F and 2'-OCH$_3$ Monomers

The following antisense strands of siRNA's were hybridized to the complementary full phosphodiester sense strand. Where the antisense strand has a TT 3'-terminus the corresponding sense strand also has a 3'-TT (deoxyT's). Bolded monomers are 2'-F containing monomers. Underlined monomers are 2'-OCH$_3$. Monomers that are not bolded or underlined do not contain a sugar surrogate. Linkages are shown in the parenthesis after the sequence.

| SEQ ID NO./ ISIS NO. | Composition (5' 3') | Features |
|---|---|---|
| 27/283546 | CUG_ CU_A_ G_CC_ UCU G_GA_ UUU G_U_.dT-3' | (OMe/F/PO) |
| 28/336240 | UUU GUC UCU GGU CCU UA_C_ U_U_ | (OMe/F/PS) |

---

What is claimed is:

1. A composition comprising a first oligomer and a second oligomer, wherein:
at least a portion of said first oligomer is capable of hybridizing with at least a portion of said second oligomer,
at least a portion of said first oligomer is complementary to and capable of hybridizing with a selected target nucleic acid,
said first oligomer is a chimeric oligomeric compound,
wherein the chimeric oligomeric compound has an internal segment comprising five consecutive nucleosides having a 2'-OCH$_3$ substituent group, and
wherein the chimeric oligomeric compound is not a gapmer.

2. The composition of claim 1 wherein said first and said second oligomers are a complementary pair of siRNA oligomers.

3. The composition of claim 1 wherein each of said first and second oligomers comprise from about 18 to about 30 linked nucleosides.

4. The composition of claim 1 wherein each of said first and second oligomers comprise from about 21 to about 24 linked nucleosides.

5. The composition of claim 1 wherein said first oligomer is an antisense oligomer.

6. The composition of claim 1 wherein said second oligomer comprises a sense oligomer.

7. The composition of claim 1 wherein at least one of said first or second oligomers has at least one phosphorothioate internucleoside linkage.

8. The composition of claim 7 wherein the at least one phosphorothioate internucleoside linkage is a terminal internucleoside linkage.

9. The composition of claim 1 wherein the 5'-terminal nucleoside of said first oligomer has a 5'-phosphate group.

10. The composition of claim 1 wherein the at least one chimeric oligonucleotide comprises a nucleoside with a 2'-F substituent group.

11. The composition of claim 1 wherein the oligomers are blunt ended.

12. The composition of claim 1 wherein at least one of said first or second oligomers has an overhang.

13. The composition of claim 1 wherein the at least one chimeric oligonucleotide comprises a blockmer.

14. The composition of claim 13 wherein the blockmer comprises an oligonucleoside having at least two consecutive nucleosides of a first type located immediately adjacent to at least one nucleoside of a second type and
wherein said nucleosides of said first type are different from said nucleosides of said second type.

15. The composition of claim 14 wherein each of said nucleosides of said first type includes a 2'-OCH$_3$ substituent group.

16. The composition of claim 14 wherein the blockmer comprises an oligonucleoside having at least three consecutive nucleosides of said first type.

17. The composition of claim 14 wherein the blockmer comprises an oligonucleoside having at least five consecutive nucleosides of said first type.

18. A composition comprising a first oligomer and a second oligomer, wherein:
at least a portion of said first oligomer is capable of hybridizing with at least a portion of said second oligomer,
at least a portion of said first oligomer is complementary to and capable of hybridizing with a selected target nucleic acid,
said first oligomer is a chimeric oligomeric compound comprising a 5'-phosphate group on the 5'-terminal nucleoside,
wherein the chimeric oligomeric compound has a segment comprising five consecutive nucleosides having a 2'-OCH$_3$ substituent group, and
wherein the chimeric oligomeric compound is not a gapmer.

19. A composition comprising a first oligomer and a second oligomer, wherein:
at least a portion of said first oligomer is capable of hybridizing with at least a portion of said second oligomer,
at least a portion of said first oligomer is complementary to and capable of hybridizing with a selected target nucleic acid,
said first oligomer is a chimeric oligomeric compound,
wherein the chimeric oligomeric compound has a segment comprising five consecutive nucleosides having a 2'-OCH$_3$ substituent group and at least one nucleoside having a 2'-F substituent group, and
wherein the chimeric oligomeric compound is not a gapmer.

20. A composition comprising a first oligomer and a second oligomer, wherein:
at least a portion of said first oligomer is capable of hybridizing with at least a portion of said second oligomer,
at least a portion of said first oligomer is complementary to and capable of hybridizing with a selected target nucleic acid,
said first oligomer is a chimeric oligomeric compound,
wherein the chimeric oligomeric compound has a segment comprising five consecutive nucleosides having a 2'-OCH$_3$ substituent group,
wherein the chimeric oligomeric compound is not a gapmer, and
wherein the composition is blunt ended.

* * * * *